(12) United States Patent
Sibello et al.

(10) Patent No.: US 10,478,649 B2
(45) Date of Patent: Nov. 19, 2019

(54) SEALANT HAVING FIREWORTHY PROPERTIES FOR USE WITH AIRCRAFT PARTS

(71) Applicant: THE PATENT WELL LLC, Fort Worth, TX (US)

(72) Inventors: Peter Sibello, Fort Worth, TX (US); Jeff Busby, Millsap, TX (US); Chad Knight, Dodd City, TX (US); Kent Boomer, Aledo, TX (US); Matt Boyd, Fort Worth, TX (US)

(73) Assignee: THE PATENT WELL LLC, Fort Worth, TX (US)

( * ) Notice: Subject to any disclaimer, the term of this patent is extended or adjusted under 35 U.S.C. 154(b) by 57 days.

(21) Appl. No.: 15/697,266

(22) Filed: Sep. 6, 2017

(65) Prior Publication Data
US 2019/0001167 A1 Jan. 3, 2019

Related U.S. Application Data

(60) Provisional application No. 62/383,889, filed on Sep. 6, 2016.

(51) Int. Cl.
*F16J 15/14* (2006.01)
*A62C 3/08* (2006.01)
(Continued)

(52) U.S. Cl.
CPC .............. *A62C 3/08* (2013.01); *F16J 15/022* (2013.01); *G01N 25/50* (2013.01); *C08G 2190/00* (2013.01); *E04B 1/948* (2013.01)

(58) Field of Classification Search
CPC .. A62C 3/08; B32B 27/00; B64C 1/12; G01N 25/50; C08G 2190/00; E04B 1/948
See application file for complete search history.

(56) References Cited

U.S. PATENT DOCUMENTS

| | | | |
|---|---|---|---|
| 5,968,615 A | 10/1999 | Schlappa | |
| 2005/0090568 A1* | 4/2005 | Stein | C08J 9/0038 521/50 |

(Continued)

FOREIGN PATENT DOCUMENTS

DE 2003-814586 * 9/2003

OTHER PUBLICATIONS

PCT/US2017/050336, International Preliminary Report of Patentability and Written Opinion, 5 pages dated Mar. 12, 2019.
(Continued)

*Primary Examiner* — Gilbert Y Lee
(74) *Attorney, Agent, or Firm* — Jackson Walker LLP

(57) ABSTRACT

Fireworthy sealants may be have a variety of compositions and be made by a variety of techniques. In certain implementations, a fireworthy sealant may include a body comprised of a cured, tacky, soft, deformable non-adhesive gel. The gel body may have an upper surface, a lower surface, and a perimeter, wherein the upper and lower surfaces of the gel body, in an uncompressed state, define a body thickness. The sealant may, in an uncompressed state, be dimensioned to fit in a first opening between a wall and an aircraft component surface and deformable when under compression to fit in a second opening, smaller than the first opening. The sealant may be flame retardant and produce low smoke density and low smoke toxicity.

30 Claims, 26 Drawing Sheets

(51) Int. Cl.
*F16J 15/02* (2006.01)
*G01N 25/50* (2006.01)
*E04B 1/94* (2006.01)

(56) References Cited

U.S. PATENT DOCUMENTS

| | | | |
|---|---|---|---|
| 2008/0233364 A1* | 9/2008 | Larson | B32B 5/28 |
| | | | 428/196 |
| 2010/0272976 A1* | 10/2010 | Ashton | B32B 27/08 |
| | | | 428/215 |
| 2011/0200784 A1* | 8/2011 | Agarwal | D01F 1/07 |
| | | | 428/97 |
| 2013/0273342 A1 | 10/2013 | Johnson et al. | |
| 2015/0069722 A1* | 3/2015 | Boyd | F16J 15/104 |
| | | | 277/651 |
| 2016/0018000 A1* | 1/2016 | Busby | F16J 15/14 |
| | | | 244/131 |
| 2016/0033043 A1* | 2/2016 | Busby | F16J 15/104 |
| | | | 244/131 |
| 2016/0131259 A1* | 5/2016 | Boyd | F16J 15/104 |
| | | | 244/131 |

OTHER PUBLICATIONS

PCT/US2017/050336. International Search Report and Written Opinion, 8 pages dated Nov. 22, 2017.

\* cited by examiner

Ds at 1.5 min: 87.0
Ds at 2.0 min: 114.0
Ds at 3.0 min: 151.0
Ds at 4.0 min: 165.0
Max Ds (first 4 min): 166.0
Max Ds Time (first 4 min): 3.59

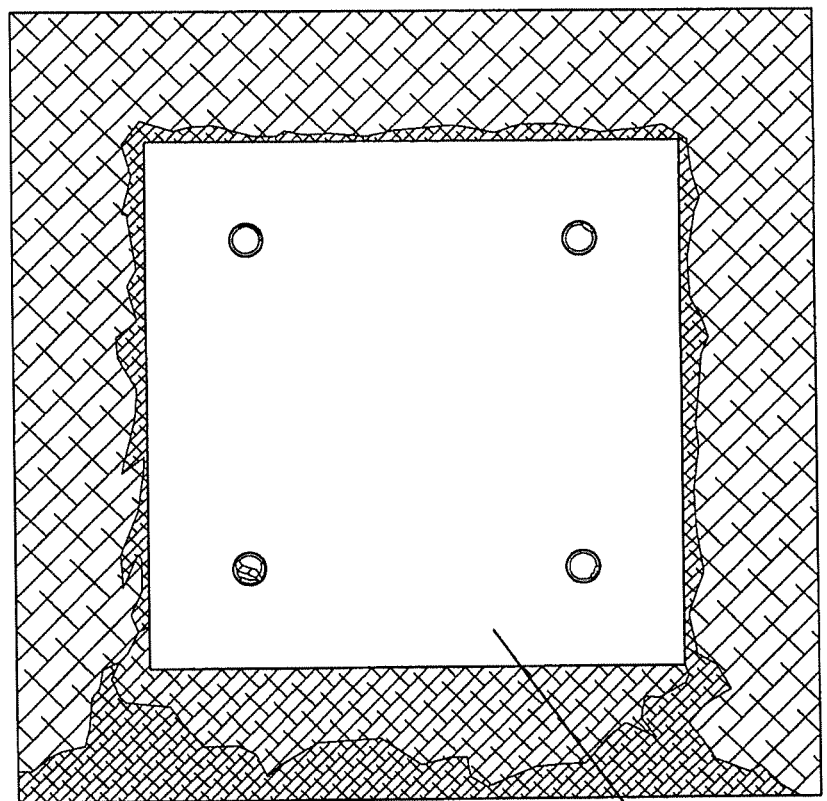
Fig. 7A  —GASKET
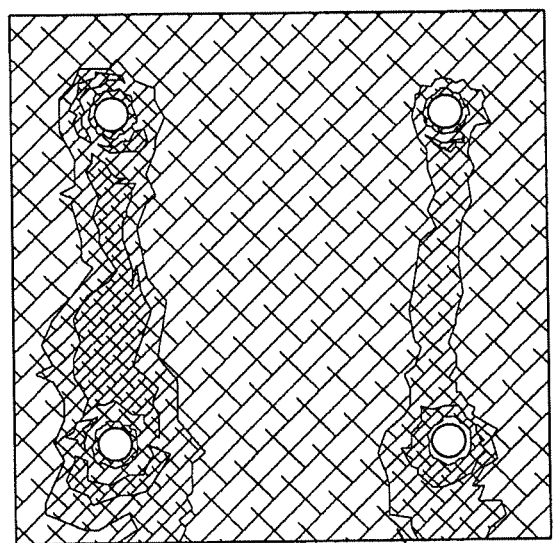
Fig. 7B  —TOP

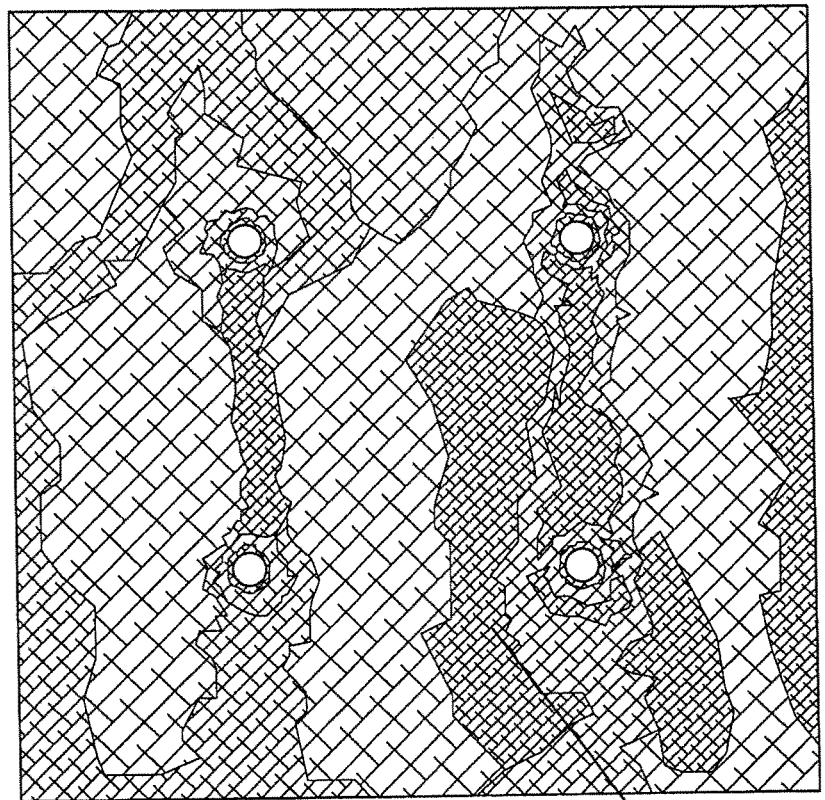
Fig. 7C — BOTTOM
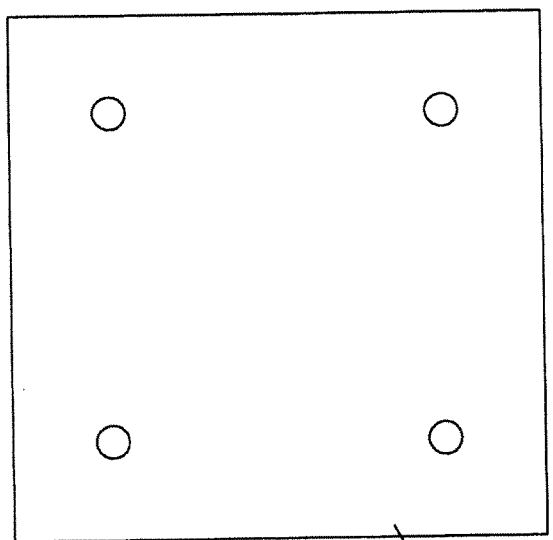
Fig. 7D — GASKET

TEST 1
Test Results: Vertical burn FAR 28.853 Appendix F, part I, (a), 1, (ii): 12 sec.

RESULTS:

|    | Burning Time (seconds) | Burning Length (inches) | Longest Burning Particle (seconds) |
|----|------------------------|-------------------------|------------------------------------|
| 1. | 0                      | 1.8                     | 0                                  |
| 2. | 0                      | 1.7                     | 0                                  |
| 3. | 0                      | 1.9                     | 0                                  |
| Avg. | 0                    | 1.8                     | 0                                  |

CRITERIA: FAR 25.853, Amdt. 25-116, FAA Form 811-25 (1-79)

|                           | (a), 1, (i)  | (a), 1, (ii) |
|---------------------------|--------------|--------------|
| Maximum Burn Time         | 15 seconds   | 15 seconds   |
| Maximum Burn Length       | 6 inches     | 8 inches     |
| Maximum Longest Burning   | 3 seconds    | 5 seconds    |
| Pass/Fail:                |              | PASS         |

Fig. 16

TEST 2

RESULTS:

|   | Ds @ 1.5m | Ds @ 4.0 m | Ds Max | Dmax time |
|---|---|---|---|---|
| 1. | 91 | 178 | 178 | 3:51 |
| 2. | 81 | 168 | 169 | 3:56 |
| 3. | 87 | 165 | 166 | 3:59 |
| Avgs. | 86 | 170 | 171 | 3:55 |

Fig. 17

TEST 3

REFERENCE: CHAMBER S/N 61900, ABD0031, AITM 3-0005, Issue 2
Draeger Tubes (DT), Potentiometry (PO),
Gas Flue Analysis (test 350)(GF)

RESULTS:

| GASSES | LIMITS @ 4 MIN | FLAMING | | | P/F | FLAMING | | | P/F | FLAMING | | | P/F |
|---|---|---|---|---|---|---|---|---|---|---|---|---|---|
| | | Result | Method | | | Result | Method | | | Result | Method | | |
| HCN | 150 PPM | 35 | ☒ | DT | P | 40 | ☒ | DT | P | | ☐ | DT | |
| CO | 1000 PPM | 562 | ☐ | DT | P | 496 | ☐ | DT | P | | ☐ | DT | |
| | | | ☒ | GF | | | ☒ | GF | | | ☐ | GF | |
| NO/NO$^2$ | 100 PPM | 50 | ☐ | DT | P | 52 | ☐ | DT | P | 51 | ☐ | DT | P |
| | | | ☒ | GF | | | ☒ | GF | | | ☒ | GF | |
| SO$^2$ | 100 PPM | 13 | ☐ | DT | P | 12 | ☐ | DT | P | | ☐ | DT | |
| | | | ☒ | GF | | | ☒ | GF | | | ☐ | GF | |
| HF | 100 PPM | *21 | ☒ | DT | P | 21 | ☒ | DT | P | | ☐ | DT | |
| HCL | 150 PPM | 4 | ☒ | DT | P | 5 | ☒ | DT | P | | ☐ | DT | |

Note: IND. = Indeterminate. Test values exceed maximum limits of Draeger tube.

\* Positive - Indicative test; HF is detected

HCN Hydrogen Cyanide
CO Carbon Monoxide
NO/NO$_2$ Nitrogen Dioxide
SO$^2$ Sulfur Dioxide
HF Hydrogen Fluoride
HCL Hydrogen Chloride

Fig. 18

SEALANT HAVING FIREWORTHY PROPERTIES FOR USE WITH AIRCRAFT PARTS

RELATED APPLICATIONS

This application claims the benefit of, and priority to, U.S. Patent Application No. 62/383,889, filed Sep. 6, 2016. This prior application is herein incorporated by reference in its entirety.

FIELD OF THE INVENTION

A sealant with flame retardant properties, low smoke density, and/or low combustion (smoke) toxicity for use with aircraft components and equipment.

BACKGROUND

Fireworthiness properties, namely, one or more of low smoke density, low-toxicity, and flame retardant properties, are important in the manufacture and maintenance of aircraft. It is a significant challenge in design, sourcing, and manufacturing to locate or develop components for manufacturing a gasket for aircraft because of the critical nature of the environment in which they are used. Soft, tacky sealants, which can be used as gaskets, have been known hereto, but these do not fulfill all fire protection standards for certain applications.

Aircraft and sealants used with aircraft are constantly thermally cycled and pressure cycled, and the sealants must maintain their effective environmental sealing properties despite such a radical variation in the environment to which they are subject. Sometimes it is hot and sometimes cold; and sometimes it is dry, or it is a damp or wet environment with a number of different chemicals. Acid rain, for example, can be corrosive especially when exposed to a metallic aircraft surface. For example, a slight pH change in rain may make it slightly acidic and corrosive especially on an aluminum aircraft exterior.

Composite parts used in aircraft construction should comply with standards related to burning behavior of the material.

Thus, it has been proven to be a challenge to design and manufacture sealants that are acceptable in a wide variety of environments over a wide temperature, pressure, and chemical range, which sealants maintain their properties and are also, in a fire, non-toxic and flame retardant (or flame resistance). Moreover, what smoke is produced should be of a low density.

SUMMARY

A properly designed part, including a gasket sealant, an injectable sealant, or a tape sealant (collectively a sealant), will help establish safety for passengers of commercial aircraft especially in event of a fire. Such sealants may be used at the interfaces of components to provide an effective and relatively fire safe seal under a variety of environmental conditions.

The fireworthiness design criteria are related to one or more of the burning behavior of materials, components, subcomponents and system parts. Fireworthiness as set forth herein refers to the passing of tests for vertical burn (a measure of flame propagation), smoke density (a measure of the smoke emitted by a material when burned) and toxicity limits (the release of noxious and/or harmful gases under flame). Fireworthiness is especially important in use with the interior of commercial aircraft.

In some embodiments, Applicant provides a sealant having fireworthy properties. A fireworthy, adhesive free sealant may include a body and a skeleton. The body may encapsulate the skeleton, the body comprising a cured, tacky, soft, deformable gel, the skeleton having multiple openings for encapsulation by the gel body, the skeleton having an upper surface, a lower surface, and a perimeter, the gel body having an upper surface, a lower surface, and a perimeter, wherein the upper and lower surfaces of the gel body, in an uncompressed state, define a body thickness, the body thickness greater than a skeleton thickness, the sealant in an uncompressed state dimensioned to fit in a first opening between the wall and component surfaces and deformable when under compression from a tightening of the fasteners to a second opening, smaller than the first opening, wherein the sealant is fireworthy.

Smoke toxicity generally tests for leftover components of halogenated flame retardants, which are harmful in an enclosed area. Smoke density is an optical test, with the material heated to a certain temperature and measure the obscuration of a light beam traveling through smoke generated in a chamber.

The gel used in the fireworthy sealant may be 100% solid (no VOCs). The fireworthy sealant may have a smoke density Ds of 200 maximum during a test period of about 4.0 minutes under AITM2-0007A, Issue 3, Airbus specification, published and distributed by Airbus Industries. The fireworthy sealant may have smoke toxicity limits of less than about: 150 PPM HCN, 1000 PPM CO, 100 PPM NO/$NO^2$, 100 PPM $SO^2$, 100 PPM HF, and 150 PPM HCl per AITM 3-0005, Issue 2, Airbus specification, published and distributed by Airbus Industries, or FAA Part 25 Appendix E-1 equivalent tests. The fireworthy sealant may pass 12 second vertical burn test according to 14 CFR, Part 25—Subpart D, § 25.853 Appendix F Part 1(b)4.

The fireworthy sealant may comprise a two-part polymer, the first part comprising a polyol and the second part comprising isocyanate, the two parts when combined curing to form the gel of the gel body. The skeleton of the fireworthy sealant, if used, may comprise a nylon or fiberglass (coated or uncoated with fire retardant) having a thickness less than about 0.033" (0.84 mm). The body of the fireworthy sealant, in some embodiments, may comprise a polyurethane gel in a molecular weight range between about 200 to about 20,000. The tackiness of the fireworthy sealant, in some embodiments, may be between about 10 and 30 psi. The fireworthy sealant may pass the 3000 hour salt fog test according to ASTMB 117. The body of the fireworthy sealant may be elastomeric and deformable under compression. The fireworthy sealant may be elastomeric and substantially recover (e.g. greater than 90%) its original dimensional configuration in a short period of time (e.g., less than one minute) after 180 days under compression between about 150 and 350 psi. The fireworthy sealant may have a smoke density Ds of 200 maximum at 4.0 minutes under AITM2-0007A, Issue 3. The fireworthy sealant may have toxicity limits of less than about: 150 PPM HCN, 1000 PPM CO, 100 PPM NO/$NO^2$, 100 PPM $SO^2$, 100 PPM HF, and 150 PPM HCl under AITM 3-0005, Issue 2. The fireworthy sealant may pass 12 second vertical burn test according to 14 CFR, Part 25—Subpart D, § 25.853(a) compartment interiors.

The fireworthy sealant may comprise a two-part polymer, the first part comprising a polyol and the second part comprising isocyanate, the two parts when combined curing to form the gel of the gel body. The gel body may comprise a cured polyurethane gel of molecular weight between about 200 and 20,000. The skeleton, in some embodiments, may be either polypropylene, nylon or woven fiberglass and less than about 0.033" (0.84 mm) thick. The volume ratio of gel body to skeleton may be in the range of about 3 to 1 to about 7 to 1. The cured hardness of the gel body may be between about 40 and 150 measured by 35 gr. cone penetrometer. The sealant body may further include a corrosion inhibiting composition, such as non-chromate inhibiting compounds.

Devices are provided for achieving an environmental seal to an aircraft assembly comprising a first part and a spaced apart second part, the two parts forming a gap, the devices comprising sealants having a skeleton and a body encapsulating the skeleton, wherein the body comprises a cured polyurethane gel, resulting from a mix of a polyol and isocyanate, the sealant having fireworthiness properties to provide the sealant for passing the following tests: wherein the sealant has toxicity limits of less than about: 150 PPM HCN, 1000 PPM CO, 100 PPM NO/NO$^2$, 100 PPM SO$^2$, 100 PPM HF, and 150 PPM HCl under AITM 3-0005, Issue 2; wherein the sealant passes 12 second vertical burn test according to 14 CFR, Part 25—Subpart D, § 25.853(a) compartment interiors; wherein the sealant has a smoke density of Ds 200 maximum at about 4.0 minutes 200 AITM2-0007A, Issue 3. The skeleton may, in some embodiments, be comprised of a nylon, polypropylene or fiberglass mesh having a thickness less than about 0.033" (0.84 mm); and the body may, in some embodiments, have a tackiness of between about 5 and 50 psi. The volume of gel/skeleton may be in the range of about 3/1 to 7/1.

The fireworthy sealants may be tacky but not adhesive to workpiece surfaces into which they come into contact. They may also be able to release cleanly (without leaving a residue) after prolonged use under compression and subject to repeated thermal and pressure cycling.

A method is disclosed for releasably, environmentally sealing a pair of opposing, gap forming or faying surfaces of aircraft parts, the method comprising the steps of: providing an adhesive-free sealant having a layer of polyurethane gel encapsulating a skeleton, the sealant having fireworthiness properties; placing the sealant in the gap between the surfaces; and closing the gap, thereby providing a substantially fluid and air tight seal between the opposed mating surfaces with the sealant substantially filling the gap; wherein the sealant has a smoke density Ds of 200 maximum at 4.0 minutes under 200 AITM2-0007A, Issue 3; wherein the sealant has toxicity limits of less than about: 150 PPM HCN, 1000 PPM CO, 100 PPM NO/NO2, 100 PPM SO2, 100 PPM HF, and 150 PPM HCl under AITM 3-0005, Issue 2; and wherein the sealant passes 12 second vertical burn test according to 14 CFR, Part 25—Subpart D, § 25.853(a) compartment interiors.

The sealant of the providing step may have a tackiness, in one embodiment of between about 5 and 50 psi or a peel strength of about 0 to 5 piw. The method may also include tightening of fasteners between the opposing surfaces until the sealant visibly deforms. The body may include a polyurethane gel with a molecular weight range between about 200 to 20,000. The sealant may pass the 3,000 hour salt fog test according to ASTMB 117. The body of sealant may be elastomeric; wherein the sealant substantially recovers at least 50% of its original dimensional configuration after compression between about 150 and 350 psi for 180 days in less than one minute. The skeleton may be nylon, polypropylene (which may be molded), or coated or uncoated woven fiberglass and less than about 0.033" (0.84 mm) thick.

In certain implementations, a non-adhesive sealant may include a body comprised of a cured, tacky, soft, deformable gel, the gel body having an upper surface, a lower surface, and a perimeter, wherein the upper and lower surfaces of the gel body, in an uncompressed state, define a body thickness. The sealant may, in an uncompressed state, be dimensioned to fit in a first opening between a wall and an aircraft component surface and deformable when under compression to fit in a second opening, smaller than the first opening. The sealant may have a smoke density less than 200 after about 4 minutes of exposure to the flame-only smoke density test in AITM2-0007A, Issue 3. The gel of the sealant may be 100% solid (no VOCs).

In some implementations, the sealant may including a skeleton encapsulated by the body. The skeleton may have multiple openings for encapsulation by the gel and have an upper surface, a lower surface, and a perimeter, wherein the upper and lower surfaces of the skeleton define a skeleton thickness, the skeleton thickness being less than the body thickness.

In certain implementations, the sealant may have toxicity limits of less than about: 150 PPM HCN, 1000 PPM CO, 100 PPM NO/NO$^2$, 100 PPM SO$^2$, 100 PPM HF, and 150 PPM HCl under AITM 3-0005, Issue 2. Additionally, the sealant may pass the 12 second vertical burn test according to 14 CFR, Part 25—Subpart D, § 25.853(a) compartment interiors. The sealant may also pass the 3000 hour salt fog test according to ASTMB 117.

The sealant may be composed of a two-part polymer, the first part comprising a polyol and the second part comprising isocyanate, the two parts when combined curing to form the gel of the gel body, and wherein the skeleton is comprised of a nylon or fiberglass having a thickness less than about 0.033" (0.84 mm). In certain implementations, the body may be composed of a polyurethane gel with a molecular weight range between about 200 to 20,000. The sealant may also have a tackiness between about 20 and 30 psi.

The sealant may quickly (e.g., in less than one minute) recover most its original dimensional configuration (e.g., greater than 90%) after compression between about 150 and 350 psi for 180 days. The volume ratio of gel body to skeleton may be in the range of about 3 to 1 and 7 to 1. The cured hardness of the gel body may be between about 40 and 150 measured by 35 gr. cone penetrometer. The body may further include a corrosion inhibiting composition.

In particular implementations, one or more sealants may be resistant to degradation upon exposure to common aviation fluids.

In a certain embodiments, the sealant is adhesive free. Adhesives create high strength bonds to the mating surfaces making clean release and reuse difficult. Sealants typically have a lower bonding strength but create substantially air and fluid tight contact with the mating surface or surfaces.

In some embodiments, a non-adhesive sealant may include a body comprised of a cured, tacky, soft, deformable gel, the gel body having an upper surface, a lower surface, and a perimeter, wherein the upper and lower surfaces of the gel body, in an uncompressed state, define a body thickness. The sealant may, in an uncompressed state, be dimensioned to fit in a first opening between a wall and an aircraft component surface and deformable when under compression to fit in a second opening, smaller than the first opening. The sealant may have toxicity limits of less than about: 150 PPM HCN, 1000 PPM CO, 100 PPM NO/NO$^2$, 100 PPM $SO^2$, 100 PPM HF, and 150 PPM HCl under AITM 3-0005, Issue 2. The gel of the sealant may be 100% solid (no VOCs).

In some implementations, the sealant may including a skeleton encapsulated by the body. The skeleton may have multiple openings for encapsulation by the gel and have an upper surface, a lower surface, and a perimeter, wherein the upper and lower surfaces of the skeleton define a skeleton thickness, the skeleton thickness being less than the body thickness.

In certain implementations, the sealant may have a smoke density less than 200 after about 4 minutes of exposure to the flame-only smoke density test in AITM2-0007A, Issue 3. Additionally, the sealant may pass the 12 second vertical burn test according to 14 CFR, Part 25—Subpart D, § 25.853(a) compartment interiors. The sealant may also pass the 3000 hour salt fog test according to ASTMB 117.

BRIEF DESCRIPTION OF THE DRAWINGS

FIGS. 7A, 7B, 7C, and 7D illustrate a test coupon after a 3000 hour salt fog test with a fireworthy gasket made according to the specification set forth herein.

FIGS. 10A, 10B, 100, 10D, and 10E are illustrations of the test apparatus probe engaging the sealant during test for tack, work of adhesion and cohesion.

FIG. 16 illustrates example test results for a vertical burn test.

FIG. 17 illustrates example test results for a smoke density test.

FIG. 18 illustrates example test results for a smoke toxicity test.

DETAILED DESCRIPTION

Figure 1:
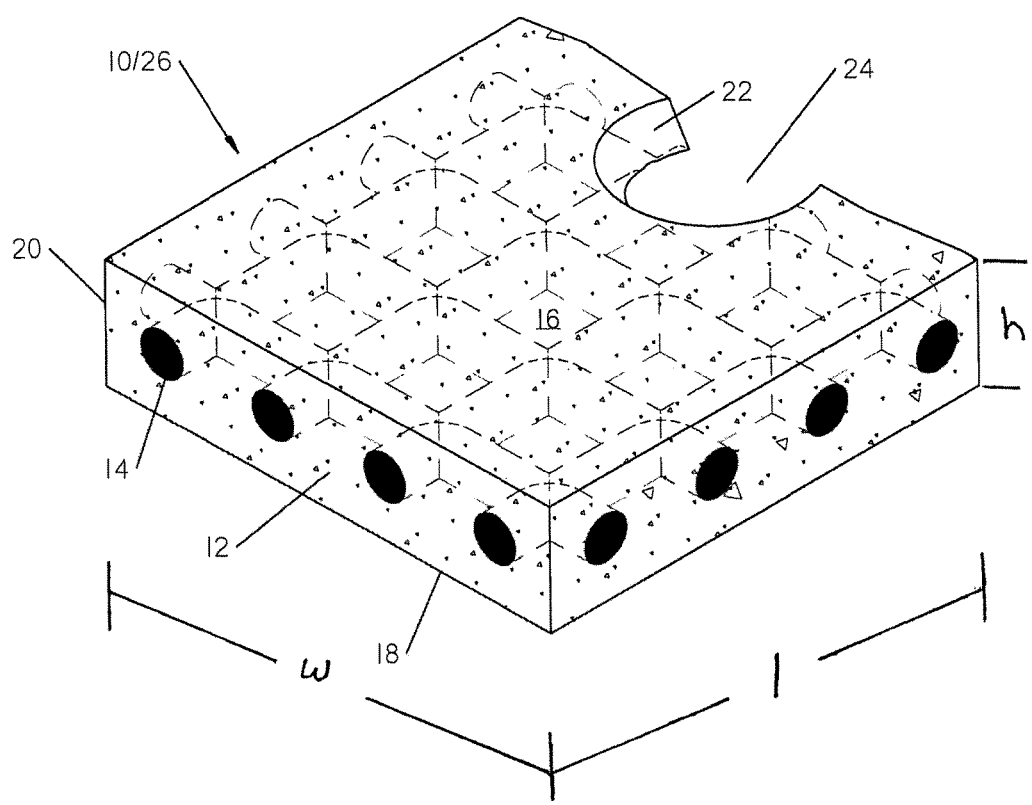
FIG. 1 is a perspective view of a gasket sealant according to the present specification.

Fireworthiness in a sealant means: the sealant (e.g., gel body and skeleton) passes all three of a flammability test, a smoke density test, and a smoke toxicity test. The flammability test is vertical burn, compartment interiors and is conducted pursuant to FAR 25.853(a) Appendix F, Part I, (a), 1, (ii): 12 sec. The smoke density test (Determination of Optical Smoke Density of Component Parts or Sub-Assemblies of Aircraft Interiors) is performed pursuant to AITM2-0007A, Issue 3 (flaming mode only). The smoke toxicity test (Determination of Specific Gas Components of Smoke Generated by Aircraft Interior Materials) is conducted in accordance with AITM3-0005, Issue 2. In certain implementations, the sealant may pass one (e.g., smoke density or smoke toxicity) or two (e.g., flammability and smoke density or flammability and smoke toxicity) of these tests.

The fireworthy sealant should be an effective, non-adhesive, environmental seal. An effective environmental seal means substantially air and moisture proof and that the sealant substantially retains, in some embodiments, a tackiness of at least about 50% of the original tackiness after 90 days under a compression of between about 150 psi-350 psi.

In some embodiments, the sealant does not include: an adhesive or an adhesive layer, foam (or air bubbles), water (less than 1% water by weight and by volume), silicone or silicone oil, leachates (under compression the leachates may cause staining to an aluminum alloy workpiece), processing oil, VOC's (volatile organic compounds) or Semi-VOC's, tackifiers or low molecular weight (liquid) materials. In some embodiments, part or all of the external surfaces of the sealant comprise the material of the encapsulating body itself (that is, no "skin" and no "adhesive layer" forming an outermost part).

The gel body of the sealant both encapsulates the skeleton and releasably bonds to opposed workpiece surfaces (unless a PTFE skin used). Typically, no adhesive layer is used as found in some prior art gaskets. In some embodiments, the skeleton may be nylon, polypropylene, or woven fiberglass, i.e., without a fire retardant coating.

Other potential skeletons include metal meshes, where mesh includes either open or closed fabrics, cloths, webs, screens, or meshes. Skeletons could also be metal wire screens or metal-plated fabric sheets. The mesh may be inherently conductive if it is formed from, for example, metal, metal alloy, graphite, or carbon. A mesh may also be constructed from monofilaments, yarns, bundles, or other fibers. A mesh may also be inherently non-conductive but made conductive by an applied coating, plating, sputtering, or other appropriate treatment of electrically conductive material.

Examples of inherently conductive materials include copper, nickel, silver, aluminum, steel, tin, bronze, and alloys of the above. Potential alloys, for example, include monel nickel and copper alloys. Other inherently conductive materials include carbon, graphite, inherently conductive polymers, plated or clad wires, silver-plated copper, nickel-clad copper, and Ferrex, tin-plated, copper-clad steel, tin-clad copper, tin-plated phosphor bronze, and fibers of any of the above materials.

Examples of inherently non-conductive materials include cotton, wool, silk, cellulose, polyester, polyamide, nylon, polyimide monofilaments or yarns. These materials may be plated, coated, or of made conductive by application of one of the "inherently conductive" materials listed above. The plating, cladding, or other coating process may be done to individual strands, to the surface after weaving, knitting, or other fabrication.

Other combinations of the above materials may also be employed. For skeleton materials having problems passing the fireworthy tests, smaller portions of the materials may be used in certain implementations.

The sealant body is tacky. Tack is a property of a sealant whereby light contact with the surface of another body brings about a condition requiring force to restore the original separated state. It is a property that will inhibit but not wholly prevent the removal of a contacting surface or surfaces, such as opposing walls of aircraft parts contacting the sealant under compression. Inherent tack means the gel possesses this property (tack) without requiring the addition of any further adhesion promoting component, or a tackifier.

Adhesive based products and gel based sealants differ on several scales. One of them is not only what their intended use is, but also in their basic structures, bonding, and physical characteristics. Adhesives provide a more permanent, rigid and durable bonding as opposed to sealants, such as gels, which are lower in strength and far more malleable. Sealants are typically not used to bond things permanently together. Adhesives have more power for holding and bonding, but sealants are good for air and water tight spaces and as gap fillers. Sealants have lower bonding strength and a higher elongation percentage than adhesives. Sealants are meant to provide a watertight seal, but are easily removable when necessary. Adhesives typically are not meant to be removed.

Applicant's fireworthy sealants when used with aircraft parts typically achieve at least three results: substantially fill a gap (little to no air or moisture) between opposing mating surfaces, form a physical barrier to fluid and gaseous migration through the gap at the sealant/workpiece surface and maintain their sealing properties over an expected lifetime under a variety of service conditions (including −65° C. to 85° C.) of at least 180 days, and up to 1.5 years, or longer.

The sealant 10 (gasket)/26 (tape) designated, SD #5, used for fireworthiness testing is a gasket (see FIG. 1) that may be made from a two-part polyurethane gel from KBS Chemical (KBS Chemical, Dodd City, Tex. (USA)), and may be about 3" long, 2" wide, about 0.040" (1.0 mm) thick (uncompressed). The gel body may be comprised of a two-part typically 50/50 mix (by volume) of a polyol and an isosynate (KBS Chemical, Part Nos. P-1025 and N-1024). The gasket is manufactured, in certain embodiments, generally, according to U.S. Pat. Nos. 6,530,577, 6,695,320 and 7,229,516 and U.S. Patent Publication Nos. 2004/0070156 and 2004/0041356, (incorporated herein by reference), with, however, the gel being as set forth herein and the skeletal material as set forth herein. A body 12, in some embodiments of cured polyurethane, may be non-reactive to aluminum and, in particular embodiments, other aircraft materials and provides a tacky outer surface that is integral to the surface—meaning, no skin is provided, the polyurethane gel body is exposed at the workpiece surface or surfaces. It may have service temperature limits of about −65° C. to 135° C. (meaning it substantially retains its functional properties) and passes 3000+ hour salt spray test (ASTM B117). In some embodiments, body 12 may be a polyurethane gel with a hardness in the range of about 40-150 on 37.5 gr. half cone penetrometer.

The skeleton used for the tests is, in some embodiments, a molded or extruded, non-knitted nylon available from Conwed of Minneapolis, Minn. (USA) as part number NL-1400, is about 0.015" thick with 20 strands per inch. A similar molded or extruded polypropylene may also be used. In particular embodiments, the skeleton is a non-knitted nylon less than about 0.033" thick, or between about 0.008" and 0.026" thick. In another embodiment, the volume ratio of polyurethane gel/skeleton ranges are in the range of about 2/1 to 7/1 more preferably 3/1 to 6/1, preferably about 4.5/1 to provide fireworthiness.

This specification describes a fireworthy gasket 10 (FIG. 1) or a fireworthy tape 26 (FIG. 2) (together "sealant"), both as noted herein comprising a body 12 and a web or skeleton 14 as seen in FIGS. 1, 1A, 2, 3A and 3B. Body 12 is typically sheet-like, or tape typically with W and L>>T, and skeleton 14 is typically bendable along its W and L axes. Body 12 may have a tacky polyurethane top surface 16 and a spaced apart, tacky polyurethane bottom surface 18. Typically, the body encapsulates the skeleton and there are no visible air bubbles. Gasket 10 or tape 26 may include outer perimeter or walls 20 and inner perimeter or walls 22 defining, optionally, fastener holes 24. In one embodiment (see FIG. 1A), a skin 30 may be interposed on one (top or bottom) or both surfaces of the body, which skin 30 may be intended to be part of the gasket, that is to say, is intended to be under compression between a platform and a workpiece. In one embodiment, skin 30 is a thin sheet of PTFE. In a preferred embodiment, there is no skin, the gel body includes the top and bottom surfaces that contact the workpiece. A release film 28 may be provided for adherence to the top 16 and/or bottom 18 surfaces, which release film prevents the tacky polyurethane surfaces from inadvertently adhering to objects prior to removal and use. Release film 28 is intended for removal prior to use between a workpiece and a platform or base, that is to say, before interposing the gasket between mating surfaces.

Figure 1A:
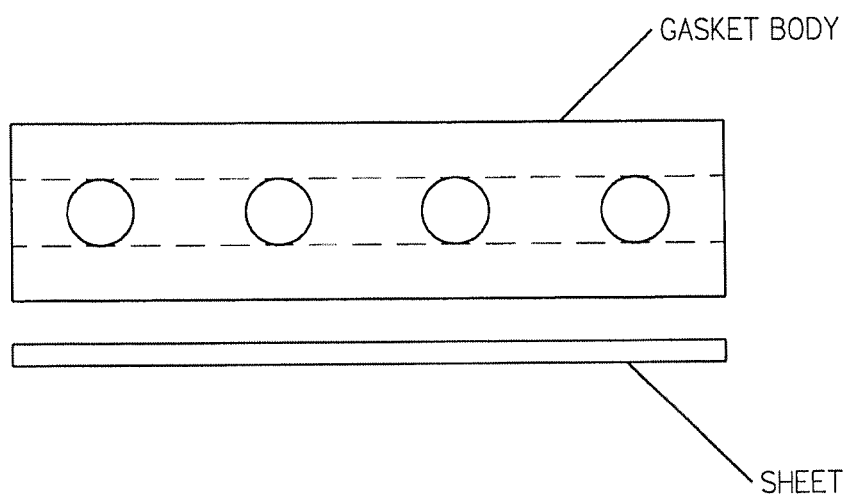
FIG. 1A is an elevational view of a gasket sealant with an impervious, tack and adhesive-free sheet on a surface thereof.

FIG. 1A illustrates a gasket having a skeleton and a skin 30 comprising a PTFE sheet. The PTFE sheet is applied to one side of the body of the gasket. The PTFE sheet sticks to the one side of the gasket. With the PTFE sheet on one side of the gasket and the other side of the gasket having a body exposed to the workpiece, for example, two aircraft parts under compression, the side of the gasket having the PTFE sheet is non-tacky to the workpiece. This then become a gasket with only a single face tacky to the workpiece. A gasket such as this may be used in embodiments where selective release to one side is desire. Another environment, where only one side of a gasket requires a good environmental seal (sticky side to the workpiece) a gasket such as the single sided sticky gasket illustrated in FIG. 1A may be sufficient. There are other types of sheets that may be sticky to the gasket and non-sticky to the workpiece, PTFE being only one example.

Figure 2:
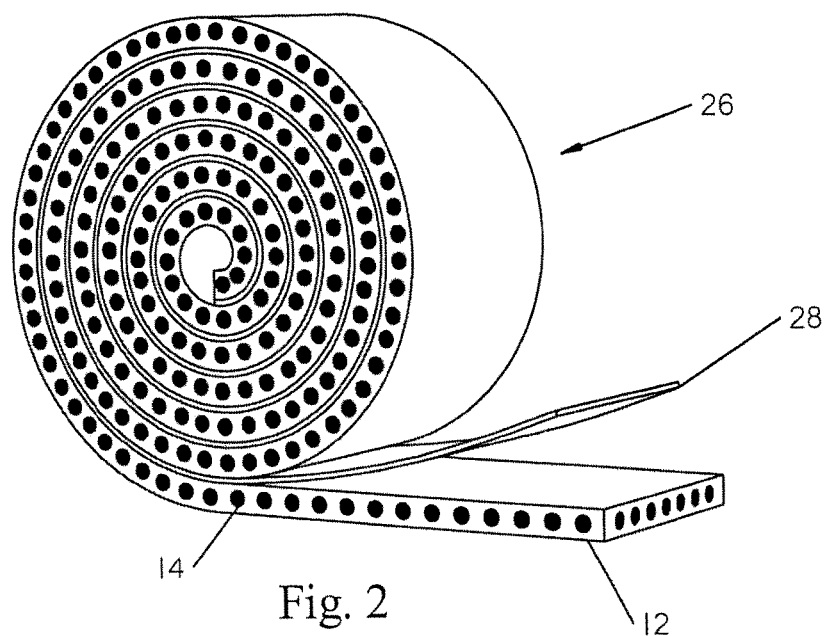
FIG. 2 shows a tape sealant according to the present specification.
Figure 3A:
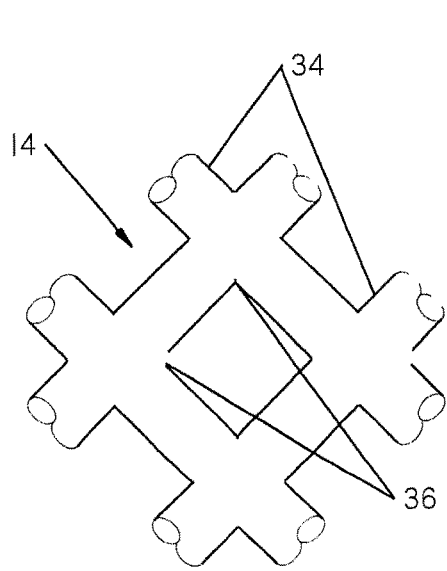
FIG. 3A and FIG. 3B are illustrations of skeletal structures that may be used in application's sealant.

Applicant provides, in some embodiments, a non-knitted, non-woven net-like skeleton 14 with multiple open pores defined by strands 34 joined at joints 36 (see FIGS. 1, 2 and 3A). In another embodiment, see FIG. 3B, the skeleton may be a woven or knitted material with strands crossing and touching instead of being joined ("fused") such as woven monofilament nylon or woven multifilament nylon 15 or woven or knitted fiberglass. In one embodiment, the sealant consists of body 12 and skeleton 14. In another embodiment, the sealant consists essentially of body 12 and skeleton 14.

Figure 3B:
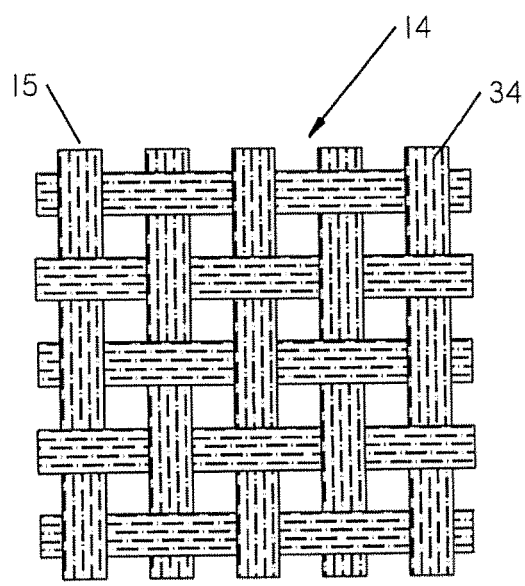

FIG. 3A shows a molded or extruded, non-metal, plastic skeleton such as a synthetic or semi-synthetic polyamide, in one embodiment, nylon. FIG. 3B shows a skeleton that is woven or knitted and may also be from the same materials and have the same properties as set forth herein.

The various gaskets, tape, and injectables of the instant disclosure may be used for numerous applications on an aircraft and, in some embodiments, a railroad car, a ship or other waterborne vessels. The aircraft uses include, but are not limited to: fuel access door gaskets, aircraft floor panel gaskets (see FIGS. 8A-8D), aircraft antenna gaskets, cargo bay, galley and surge plate environments. Injectables may be used in seat track channels (See FIG. 15) or where wires or conduits penetrate an aircraft wall (See FIGS. 13A-B).

Applicant has tested for flame travel and smoke density on fiberglass mesh of about 0.015" (0.38 mm) thickness that is used for screen purposes, such as in windows and doors. It appears to generate significantly more smoke than coated fiberglass mesh. Wire mesh, such as a woven metallic aluminum or other metal skeleton, may be used, such as 0.11 to 0.25 mil aluminum alloy. A woven nylon cloth would work as a suitable skeleton, based on initial tests. Both of these products may, in some embodiments, be in the gel to mesh ratios indicated. Other example skeleton materials include nylon, polypropylene, polyethylene, and PTFE.

Figure 4:
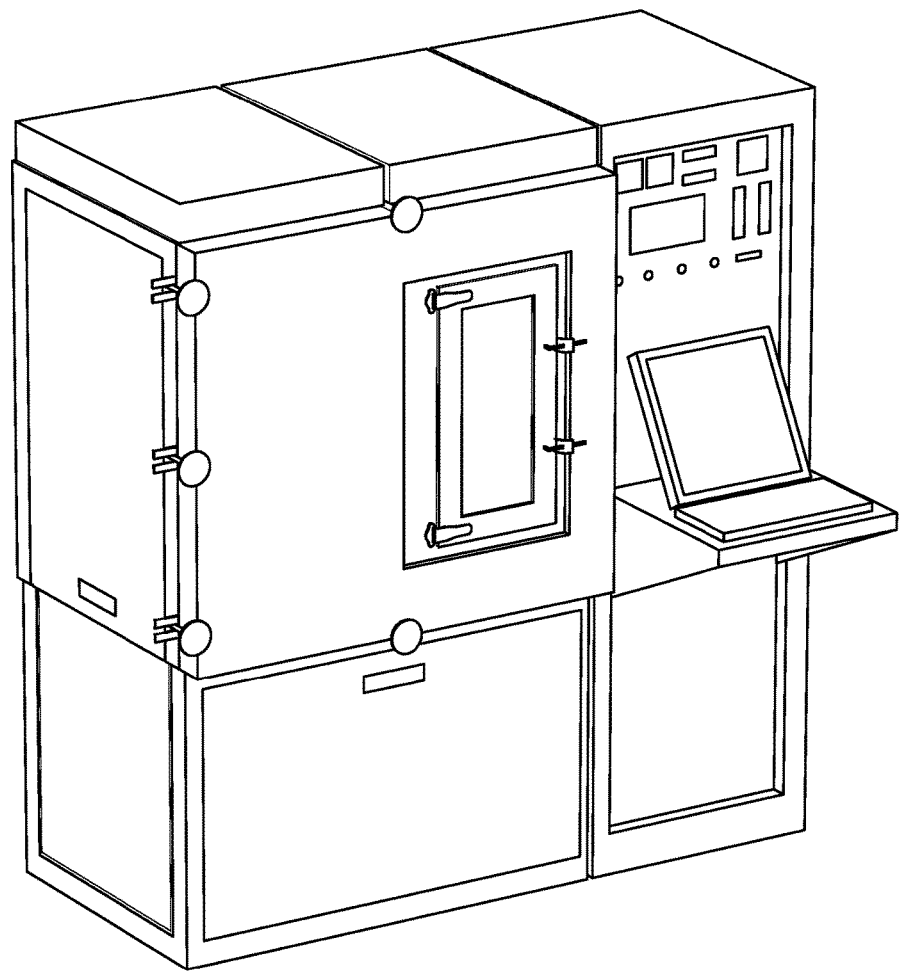
FIG. 4 illustrates an apparatus for testing smoke density and smoke toxicity.
Figure 4A:
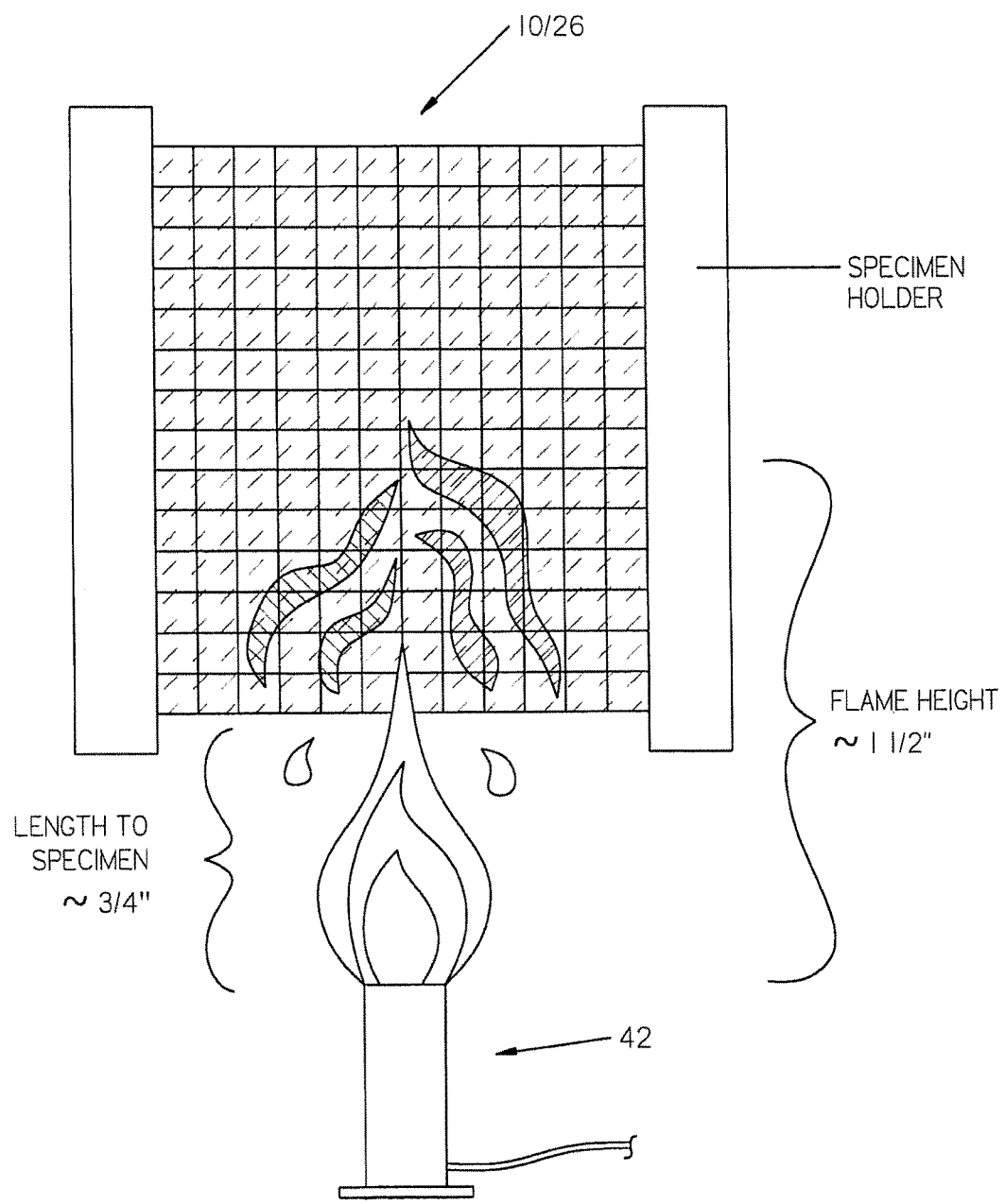
FIG. 4A illustrates a sealant undergoing vertical flammability testing.

FIG. 4A illustrates Example 1, wherein Applicant provides a sealant 10/26 that in the Vertical Flammability test is approximately 3" by 12" about 0.099 oz. In the Smoke Density and Smoke Toxicity tests, the sealant 10/26 is 2.9" by 2.9" and weighs about 0.023 oz.

Figure 12:
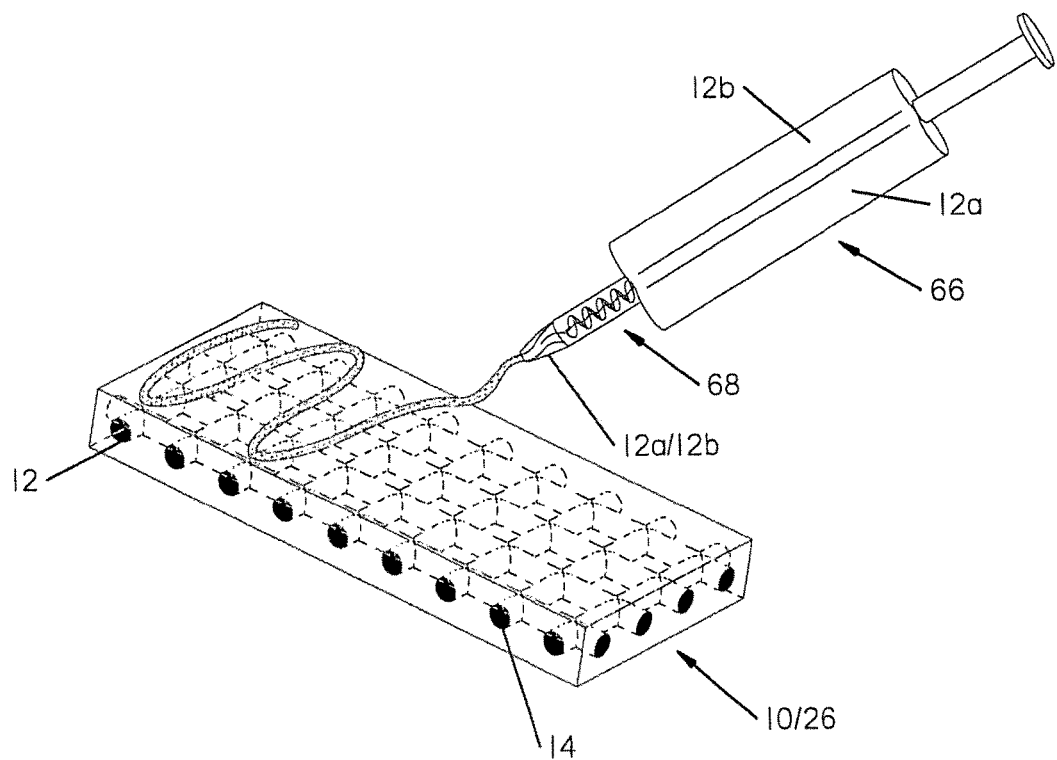
FIG. 12 illustrates a manner of making a sealant described herein.

FIG. 12 illustrates sealants may be made using an applicator 66, such as a 200 mil dual component cartridge for dispensing sealants, such as a Power Push 7000 by Meritool. Applicator 66 comprises two compartments, one for receiving a first part, such as a polyol 12a, Part No. KBS P-1025, and a second for receiving a part, a urethane component provided by an isocynate 12b, such as Part No. KBS U-1024. The two parts may mix in nozzle 68 thoroughly and flow as a syrupy mass uncured gel mix 12a/12b onto a support surface, such as a flat glass table, with a release film thereon, so that they coat and encapsulate mesh 12 and cure (between about 30 and 90 minutes) for removal from the release sheet. The sealants tested 10/26 may be about 0.0365 oz. per square inch at 44 mil thickness. This corresponds to a weight of about 0.0338 oz. per square inch for the gel and about 0.0027 oz. per square inch for the mesh. The mesh used was the Conwed mesh referenced herein.

The gel was poured to about 44 mil thickness. The manufacturing steps are substantially as set forth in U.S. Pat. Nos. 6,530,577; 6,695,320; 7,229,516; and US 2003/0234498. The gel mix 12a/12b is best applied with a crisscross or zigzag pattern overlapping the ends of the skeleton, which excess gel, after curing, can be cut with a razor and removed or otherwise trimmed. Any visible bubbles should be worked out with fingers after laying on a release sheet. Excess material may be squeegeed off before curing.

Testing on similar gaskets placed under a torque of between about 15 and about 35 inch pounds for over six months have shown clean separation between two aluminum alloy aircraft pieces and showed that the sealant recovered to about 40% to 90% of its original thickness and shape, did not dry out, maintained its structural integrity and other chemical and physical properties including but most of its tackiness, and provided an effective environmental seal. In certain embodiments, the sealant will recover the majority of its original shape (e.g., greater than 75%) in less than three minutes, and in some embodiments, the sealant may recover most of its shape (e.g., greater than 90%) and/or recover its shape in less than one minute. In particular implementations, the gasket may recover close to all of its original shape (e.g., greater than 99%). Moreover, the surface tackiness allowed it to maintain its reusability, allowing multiple releases and resealing of the same sealant.

Figure 13A:
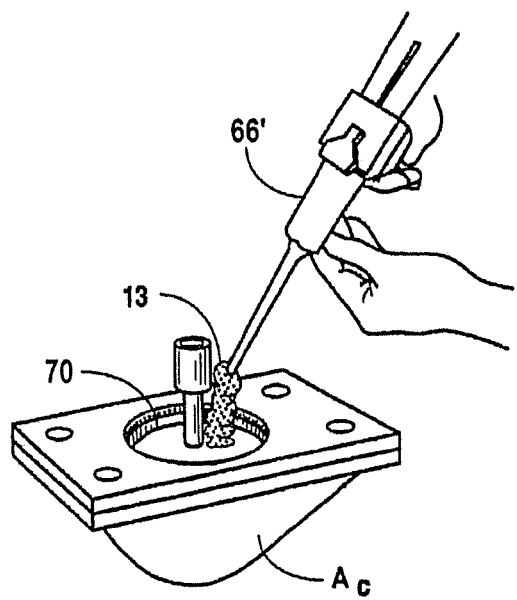
FIGS. 13A-B illustrate examples of an injectable sealant according to the present specification.
Figure 13B:
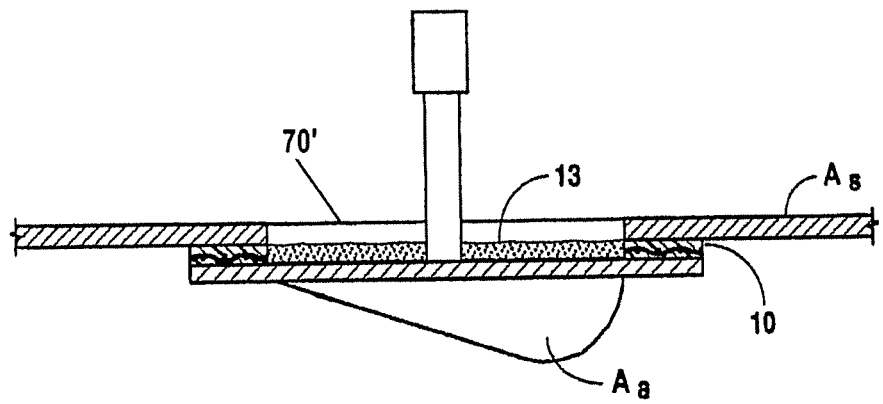

FIGS. 13A-B illustrate examples of an injectable sealant 13. Sealant 13 may be similar in composition to the body of gasket 10. For example, sealant 13 may be a two-part, polyurethane gel (e.g., mix of polyol and isocyanate). Sealant 13 typically does not includes a skeleton, however. Sealant 13 may be fireworthy (i.e., pass all three tests), pass two or more of the fireworthy tests (e.g., flammability and smoke density), or just pass one of the fireworthy tests (e.g., smoke density).

In FIG. 13A, sealant 13 is being applied from a two-part applicator 66' to a cavity 70 formed by an aircraft component Ac. Although cavity is shown here as being fairly wide compared to its depth, cavity 70 may generally take the shape of any partially enclosed structure (e.g., a basin, a gap, or a crack). As illustrated, sealant 13 may be applied directly into cavity. Due to its viscosity, sealant 13 may self level (e.g., fill the cavity from the bottom up). Depending on how much sealant is applied, sealant 13 may fill all or part of cavity 70. After application, sealant 13 will cure (e.g., form in place) in cavity 70, forming a seal to the edges of the cavity and around conduit 72.

FIG. 13B shows two-part sealant 13 cured in a cavity 70', formed by an aircraft antenna Aa, gasket 10, and an aircraft skin As. As mentioned above, due to its viscosity, sealant 13 has self-leveled in cavity 70'.

Figure 15:
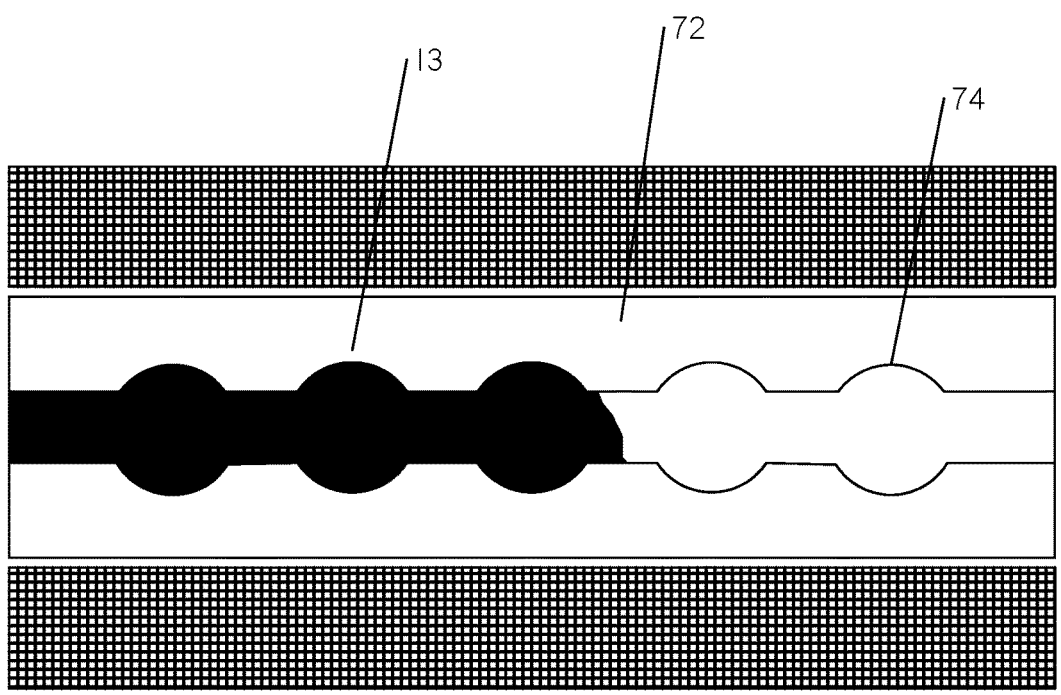
FIG. 15 illustrates another example use of an injectable sealant.

In FIG. 15, sealant 13 has been applied to an aircraft seat track 72. Seat track 72 may, for example, be made of an aluminum alloy and, as illustrated, includes a channel 74 in which lower mounts for aircraft seats may be inserted and adjusted. Without some type of sealant, channel 74 may remain open catch debris. Sealant 13 may be applied from a two-part applicator to channel 74. Due to its viscosity, sealant 13 may self level (e.g., fill the cavity from the bottom up). Depending on how much sealant is applied, sealant 13 may fill all or part of channel 74. After application, sealant 13 will cure (e.g., form in place) in channel 74, forming a seal to the sides and bottom of the channel.

Sealant tested was 2"×3" (Smoke Density and Toxicity) sealant designated SD #5 with a thickness about 0.040" (1.0 mm). It has a thin nylon mesh skeleton or carrier about 0.015" (0.38 mm) thick, part NL-1400 (Conwed, www.conwedplastics.com) white, pattern/Design 20. The body is composed of a two part cured polyurethane gel, 50/50 mix of polyol and isocynate, KBS Chemical, Part Nos. U-1024 (urethane) and P-1025 (polyol). This sealant passed all three fireworthy tests.

Fire Retardant Chemicals for use with polyurethane include hydrated metal compounds and phosphorous flame retardants. In the present invention, the flame retardant added to the polyurethane gel is not particularly limited, but a halogen-free flame retardant which does not produce a toxic halogen gas is preferred.

Examples of hydrated metal compound based flame retardants include aluminum hydroxide, aluminum oxide hydroxide, magnesium hydroxide, calcium hydroxide and the like. Examples of the inorganic compound based flame retardant include antimony compound, zinc borate, zinc stannate, molybdenum compound, zinc oxide, zinc sulfide, zeolite, titanium oxide, nano filler (montmorillonite (MMT), nano hydrated metal compound, silica), carbon nanotube, calcium carbonate and the like.

Examples of phosphorus flame retardants include phosphates, aromatic condensed phosphates, ammonium polyphosphates and the like. Specific examples of the phosphate include triphenyl phosphate, tricresyl phosphate (TCP), cresyl diphenyl phosphate (CDP), 2-ethylhexyldiphenyl phosphate, triethyl phosphate (TEP), tri-n-butyl phosphate, trixylenyl phosphate, xylenyl diphenyl phosphate (XDP), triphenl phosphate (TPP), isopropylated triphenyl phosphate (IPTPP), tris (p-t-butylphenyl) phosphate (TBPP), and the like. Specific examples of the aromatic condensed phosphate include resorcinol bisdiphenyl phosphate, bisphenol A bis (diphenyl phosphate), resorcinol bisdixylenyl phosphate and the like. Specific examples of the ammonium polyphosphate include ammonium polyphosphate (APP), melamine-modified ammonium polyphosphate and coated ammonium polyphosphate. Here, the coated ammonium polyphosphate is obtained by coating or microcapsulating ammonium polyphosphate with a resin to enhance water resistance. The phosphate, aromatic condensed phosphate and ammonium polyphosphate can be used concurrently.

Examples of silicone flame retardants include dimethylsilicone, amino-modified silicone, epoxy-modified silicone and the like.

Examples of nitrogen compound based flame retardants include hindered amine compounds, melamine cyanurate, triazine compounds, guanidine compounds and the like.

Examples of organic metal compound based flame retardants include copper ethylenediaminetetraacetate, calcium perfluorobutanesulfonate and the like.

Examples of proprietary flame retardant mixtures include: Emerald Innovation NH-1 from Great Lakes Solutions of Middlebury, Conn. (USA), Fyrol HF-5 from ICL Industrial Products of Beer-Sheva, South (Israel), Firemaster 500® or 600® (Halogenated) from Great Lakes Solutions, Exolit AP-740 from Clariant of Muttenz, Basel-Country (Switzerland), Antiblaze PR82 from Albemarle Corporation of Charlotte, N.C. (USA).

Other examples of flame retardants include: Expandable graphite, melamine, phosphoric acid, Borax, clays, mesophorus silicate.

One or more kinds of the flame retardants may be used typically as powder added in a mixture on the polyol side or the isocyanate side or both sides (that is, before the two are mixed in applicator nozzle). While the amount to be used may be varied depending on the kind of the flame retardant or the desired physical characteristics of the resulting sealant, in some embodiments, it is preferably not less than about five parts by weight, more preferably not less than ten parts by weight, particularly preferably not less than twenty parts by weight, relative to 100 parts by weight of the total polyol plus isocyanate (gel) mix 12a/12b. Here, the powder may be premixed in the polyol and isocyanate the two parts mixing in an applicator nozzle. In one embodiment, the two parts will set up (to about 90% final hardness) in about 30 minutes upon mixing.

Test 1

FIG. 16 illustrates example test results for a vertical burn test in accordance with FAR 28.853 Appendix F, part I, (a), 1, (ii): 12 sec. (same as ABD 0031), FIG. 4A illustrates the test apparatus and test setup.

Vertical burn test is used for cabin and cargo compartment materials on aircraft may utilize a Bunsen burner 42. This test is intended for use in determining the resistance of materials to flame when testing according to 60 second and 12 second vertical Bunsen burner tests as specified in FAR 25.853 and FAR 25.855. Ignition time is the length of time the burner flame is applied to the specimen 10/26 and may be either 60 or 12 seconds for this test. The flame time is the time in seconds that the specimens continue to burn after the burner flame is removed from beneath the specimen. Surface burning that results in a glow but not in a flame is not included. Drip flame time is the time in seconds that any flaming material continues to flame after falling from the specimen to the floor of the chamber. If no material falls from the specimen, the drip flame time is reported to be zero seconds and the notation "No Drip" is also reported. Burn length is the distance from the original specimen edge to the farthest evidence of damage to the test specimen due to that area's combustion including areas of partial combustion, charring or embrittlement, but not including areas sooted, stained, warped or discolored, nor areas where material has shrunk or melted away from the heat.

Test 2

Figure 5:
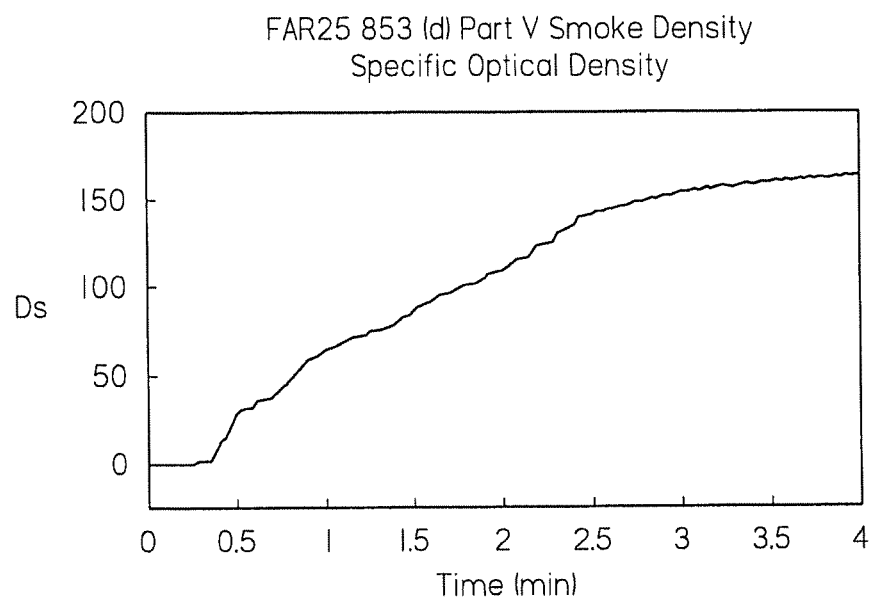
FIG. 5 and FIG. 6 illustrate Smoke Density results of the same products subject to the flammability and Smoke Toxicity tests.
Figure 6:
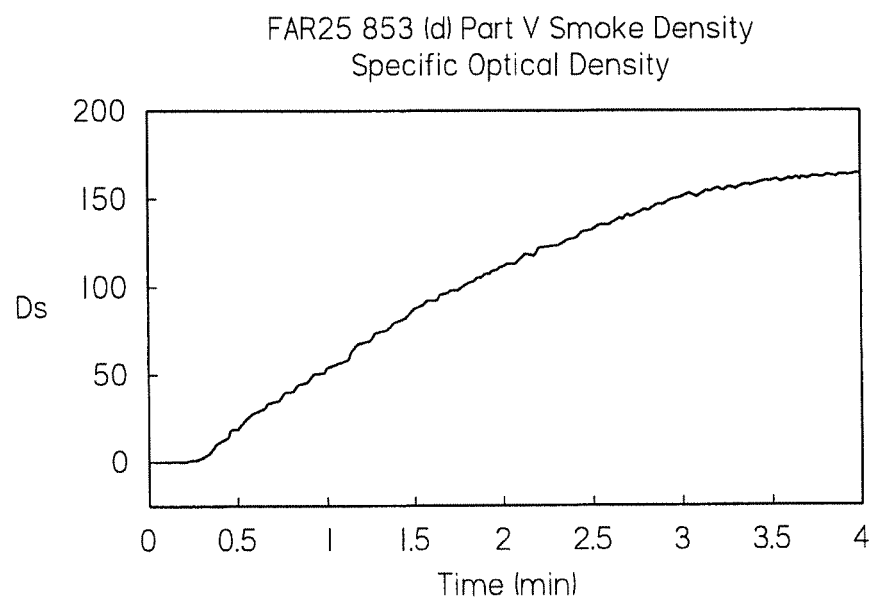

FIG. 16 illustrates example test results for a smoke density test. FIGS. 5 and 6 graphically illustrate the results.

FIGS. 5 and 6 are graphs for specific optical density versus time. Specific optical density is a dimensionless measure of the amount of smoke produced per unit area of a material when it is burned. In this test, the maximum value of Ds that occurs during the first four minutes of a test, Dm is reported. A photometric system including a microphotometer and a photomultiplier is typically used in a smoke density chamber. A recording device is used to record the percentage of light transmission for optical density versus time during the test.

The test chamber, radiant heat furnace, heat flux density gauge, specimen holders, photometric system and multidirectional pilot burner, etc. are used in the manner as defined in the test specifications. The test chamber may be a square-cornered box, with inside dimensions about 914 mm in width, 610 mm in depth, and 914 mm in height, and a sealing door that allows a small positive test pressure to be developed. The inside surface of the test chamber may be porcelain-enameled metal (e.g., steel) or equivalent coated metal that is resistant to chemical attack and corrosion.

The photometric system capable of detecting light transmittance values of 1% minimum to an accuracy of 0.03% may be used. The system may include of a light source (e.g., an incandescent lamp in a sealed, light tight box) and a photomultiplier mounted vertically, with a photomultiplier microphotometer that converts the photomultiplier tube output either to intensity and/or optical density, with a strip chart recorder or other suitable recording means to record light transmission versus time. The light source may have a light brightness temperature equivalent to about 2200 K and have optics to produce a vertical beam of collimated light about 38 mm in diameter. The photomultiplier tube may also be mounted in a light-tight box, but located above the chamber directly opposite the light source.

The pilot burner may of a multiple flamelet type with six tubes that are fed through a common manifold with a filtered, oil-fee air at a flowrate of about 500 $cm^3$/min and at least 95% purity propane at a flow rate of about 50 $cm^3$/min, both flow rates referenced to 23° C. and 1013 hPa. The tubes may each have an inside diameter of about 1.4 mm and an outside diameter of about 3.2 mm, and the manifold may have an outer diameter of about 6.4 mm. The tubes and the manifold may be made of stainless steel.

The ends of two of the tubes may be perpendicular to the exposed face of the specimen, the ends of two of the other tubes may be at a 45 degree angle to the ends the first two tubes, and the ends of the other two tubes may be at a 90 degree angle to the ends of the first two tubes (e.g., in to the trough of the specimen holder). The pilot burner may be centered in front of and parallel to the specimen. The ends of the pilot burner's tubes that are perpendicular to the exposed face of the specimen may be positioned about 6.4 mm from the face of the specimen and 6.4 mm from the bottom edge. The tubes may generate flamelets with a visible part about 6 mm long and a luminous inner cone about 3 mm long.

The specimen holder may consist of a stainless steel frame, a backing made of insulation millboard, and a spring and retaining rod to secure the specimen in place, which may be about 75 mm×75 mm. The specimen holder may expose about 65 mm×65 mm of the specimen face and include a trough to catch and retain dripping material on its bottom front. The specimen may be wrapped in aluminum foil (e.g., dull side inward) except of the exposed face. The specimen may be conditioned to about 23° C. at about 50% relative humidity for 24 hours before the test.

Smoke density Ds may be calculated according to the following:

$$D_s = \frac{V}{L*A} \text{Log}_{10} \frac{100}{T_t}$$

Where:
  $D_s$=optical smoke density
  V=chamber volume
  L=light path length
  A=exposed specimen area
  Tt=percent light transmission at the time t in minutes
  $\text{Log}_{10}(100/T_t)$=optical density at time t.
Smoke density can be an average density over several samples (e.g., three).

Test 3

FIG. 18 illustrates example test results for a smoke toxicity test.

In general, smoke and toxicity gases should be harmless and not released in significant quantities.

In a Smoke Density Chamber, gaseous/volatile test products are drawn from the chamber at any time for analysis. This test method is used for evaluating materials or constructions used in the interior of aerospace vehicles, but may be utilized for other applications as specified in applicable procurement and regulatory documents. It is used to measure and describe the properties of materials, products or assemblies in response to heat and flame under controlled laboratory conditions. Results of this test may be used as elements of a fire risk assessment which takes into account all of the factors which are pertinent to an assessment of the fire hazard of a particular end use. One NBS Smoke Density and Smoke Toxicity chamber that may be used for these tests is Govmark Model SD-2 (see FIG. 4).

Test 4

Test Results: Salt Fog (corrosion resistance)

The Salt Fog Test (FIGS. 7A, 7B, 7C, and 7D) is a standard corrosion test ASTMB 117 and is used to verify corrosion resistance of sealants. The appearance of corrosion products, such as oxidized aluminum, is evaluated, typically visually, after a predetermined period of time, for example, 3000 hours. The apparatus uses typically a closed cabinet or chamber wherein a salt water (5% sodium chloride) solution is atomized by means of spray nozzles. This produces a dense salt water fog mist or spray in the chamber and subjects the test coupon with specimen 10/26 to a severely corrosive environment. In FIGS. 7A-7D, the coupon is 2 inches by 3 inches made according to the gel body and skeleton set forth herein with respect to the fireworthiness properties and was exposed to 3000 hours of salt fog testing. FIGS. 7A and 7D illustrate the protected portions of the aluminum coupon and the visible absence of the corrosive oxidation (substantially clear) that is seen in the mottled look (oxidized aluminum) of the exposed areas of the coupon. This is consistent with effective environmental sealing. Moreover, after such exposure, the tackiness between the aluminum and the sealant was at least about 50% or greater than the initial tackiness.

Test 5

This establishes Applicant's standard test method for evaluating the tack of polyurethane gel sealant products, and work of adhesion and cohesion.

Test Assembly

Figure 9A:
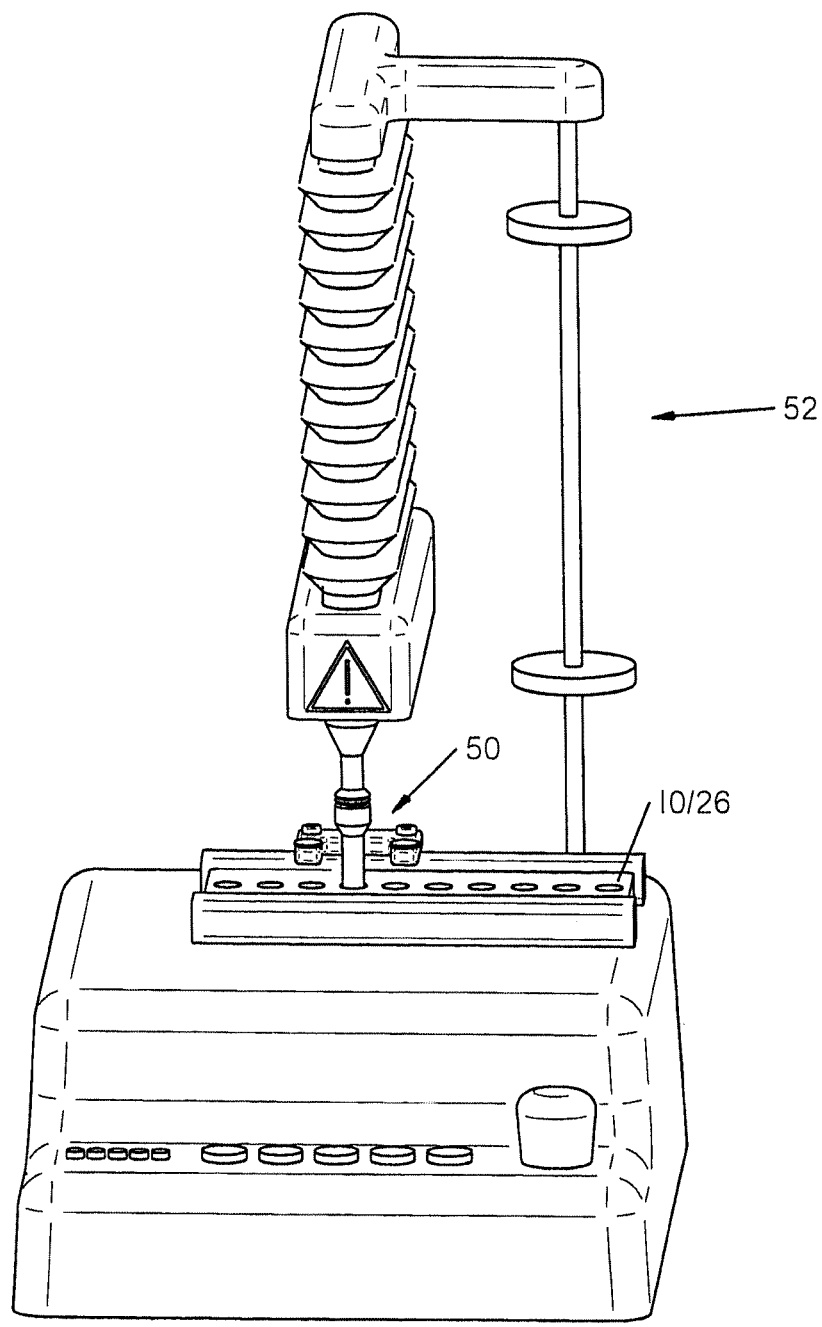
FIGS. 9A, 9B, and 9C illustrate an assembly and procedure to test physical characteristics of Applicant's sealant.
Figure 9B:
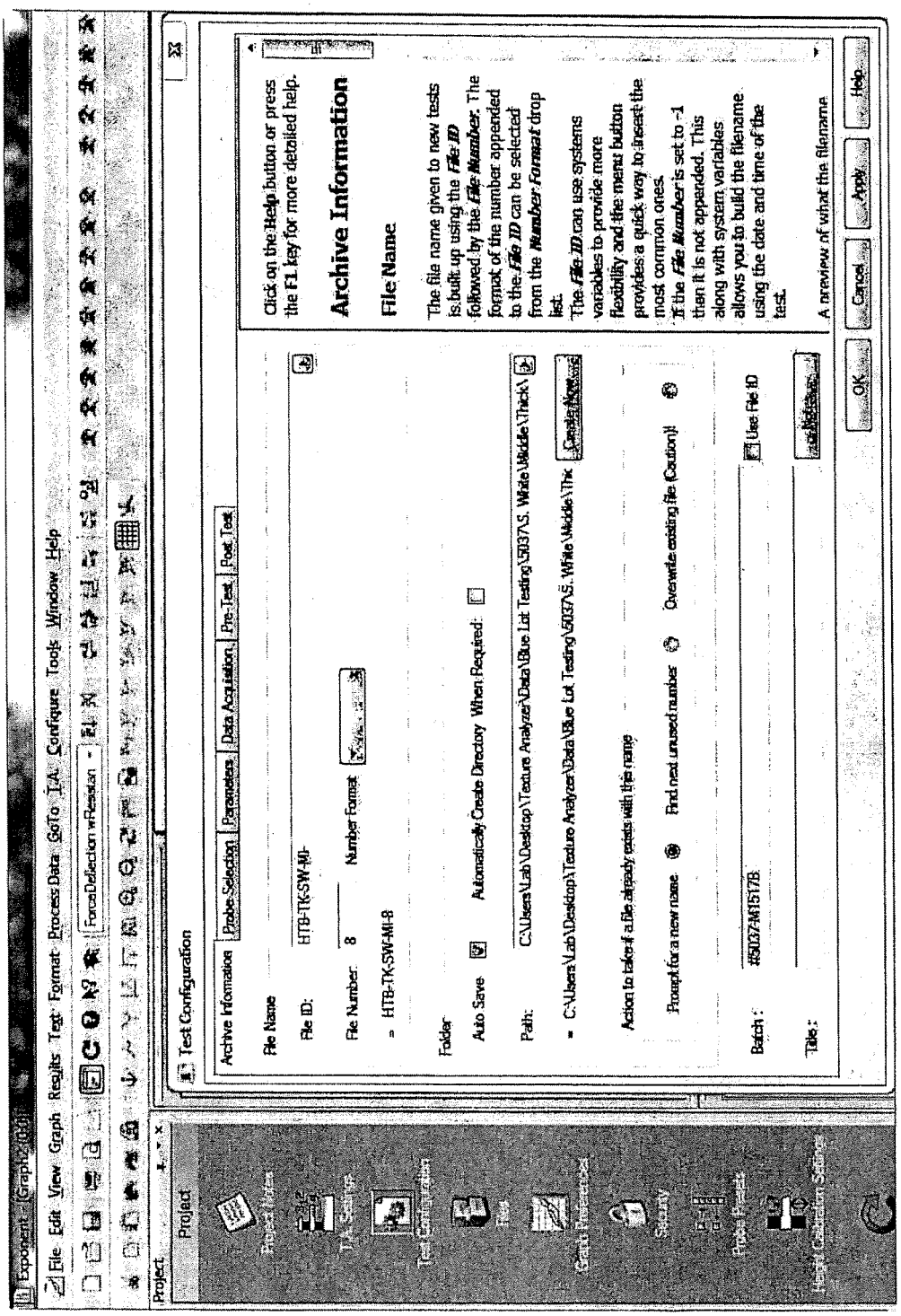
Figure 9C:
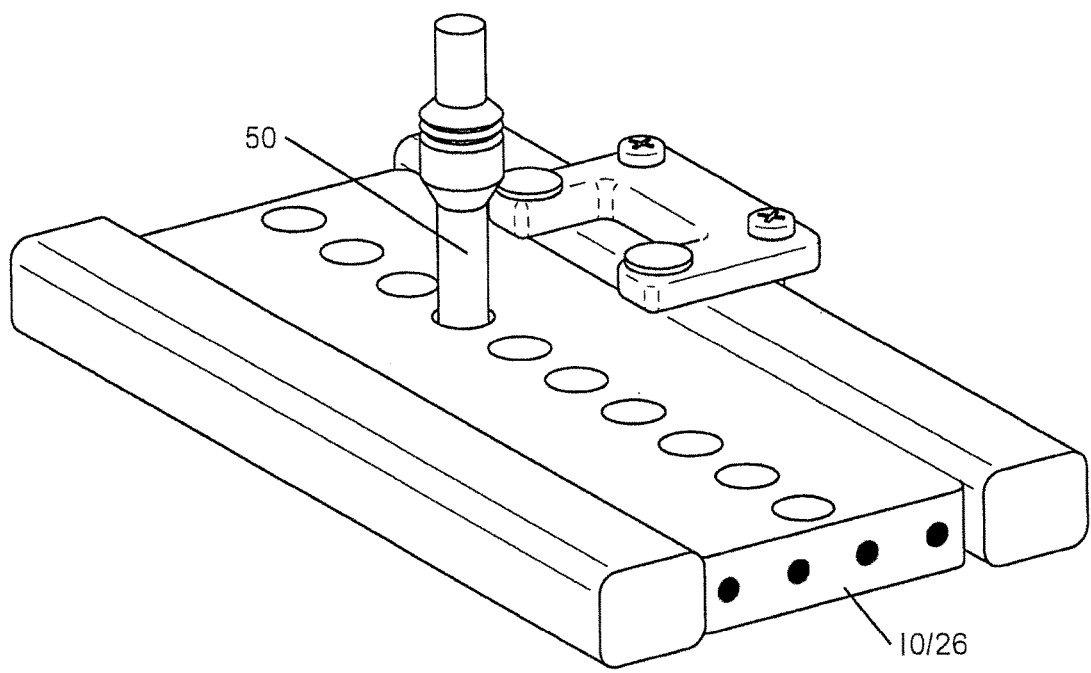

This test assembly (see FIGS. 9A, 9B, and 9C) consists of a test specimen 10/26. The test specimen is typically a 1"×6" sample of a polyurethane gel sealant material. The test specimen is tested at a temperature of 73.4±3.6° F.

Figure 10A:
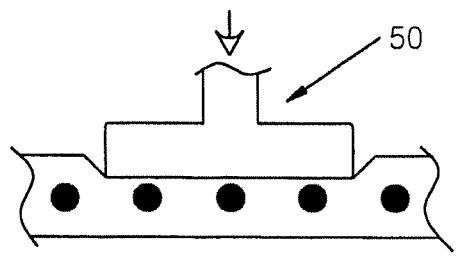

Texture Analyzer is a machine 52 that measures a number of variables, including tack, work of adhesion and cohesion of the sealant surface, when a probe moves upward from a downward deflected surface position, caused by probe 50. Applicant uses a Texture Technologies TA.XT plus with a 50 kg load cell (Texture Technologies, Hamilton, Mass., see texturetechnologies.com). See FIGS. 10A and 100 for Applicant's typical machine setup. The calibration weight is a precision mass of 200 gr. used for calibrating the load cell.

Procedure

Open the Exponent program, select a user, and click OK.

Calibration Procedure: Three calibrations shall be done before testing—height, force, and frame stiffness.

Height: To calibrate height, clear the texture analyzer of any testing materials. Click T.A.>Calibrate>Calibrate Height, enter the following values: Return Distance—10, Return Speed—10, Contract Force—1000, and then click OK.

Force: To calibrate force, clear the texture analyzer and the calibration platform of any testing materials. Click T.A.>Calibrate>Calibrate Force>Next, enter the weight of the calibration weight to be used, place the calibration weight on the calibration platform, click Next, remove the calibration weight, and flick Finish.

Frame Stiffness: To calibrate frame stiffness, clear the texture of any testing materials and ensure the proper load cell is installed. Click T.A.>Calibrate>Calibrate Frame Stiffness, enter Max Force—90% of the load cell capacity and Speed—0.01, click OK, and click OK again.

Figure 10B:
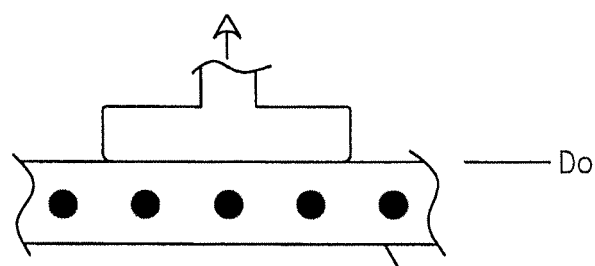

Testing Procedure: To open the project, click File>Project>Tack. Click the test configuration button and enter the name of the test in the Input File ID box, typically with the following format: Name of material—thick/thin side—Person who show the material—Front, Middle, End section of the table (for example, HTB-TN-SW-EN-). Enter the batch information in the Batch box typically with the following format: #Lot Number-Carrier Lot Number (for example, #5037-M1517B). Ensure that the AutoSave is checked and the file path is correct so that it will save to the proper folder (see FIG. 10B for typical test configuration). Remove release film on side of sample to be tested and apply the sample to the test specimen panel. Slide the test specimen panel into the base unit and tighten down in the spot to be tested. Clean the probe tip with a paper towel moistened with isopropyl alcohol. To begin the test, click Run Macro>Yes.

Figure 10C:
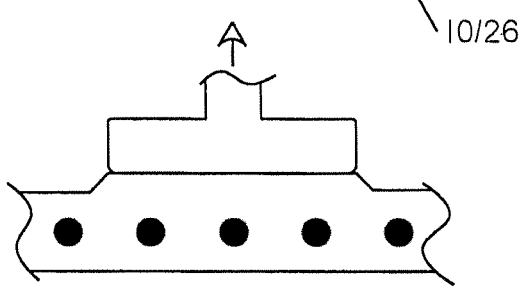
Figure 10D:
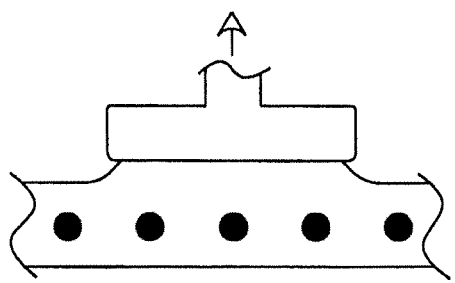
Figure 10E:
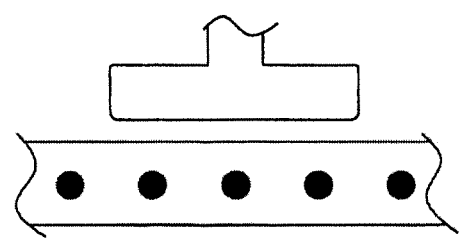
Figure 11A:
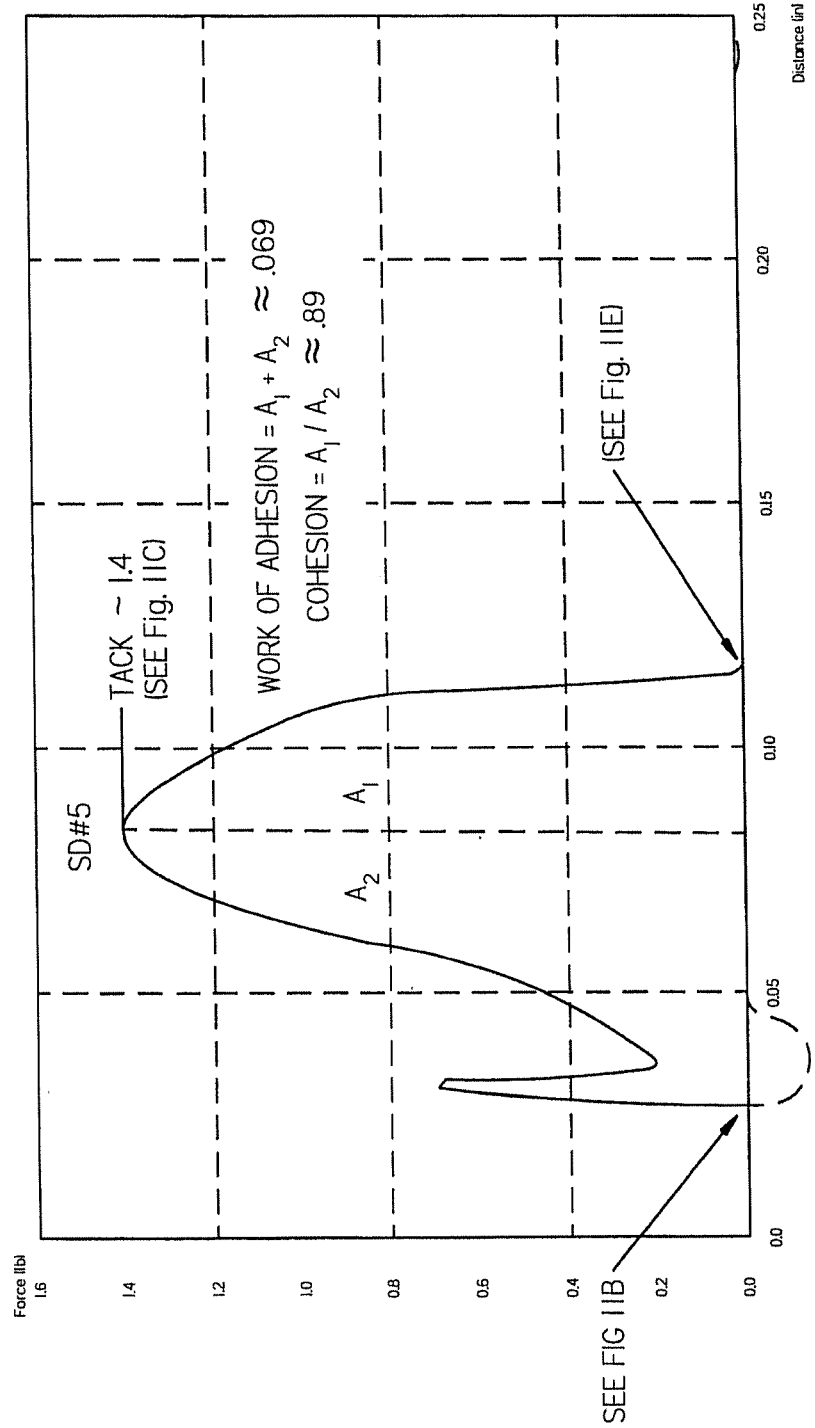
FIGS. 11A and 11B are graphs of the results of FIGS. 10A-10E tests.

The test shown in FIG. 9 Series, 10 Series, and 11 Series is for measurement of: tack, work of adhesion and cohesiveness. Force is measured as the probe goes up from the initial position (FIG. 10C). The foot of the probe (silver coated stainless, area~0.06 sq. in.) is pressed into the material (FIG. 10A) a certain distance at a certain speed and then retracted at that same speed. The force is measured on the upward retraction stroke only (FIGS. 10B-10E) to measure the "tack" of the material. Tack is the maximum point on the force vs displacement curve, the peak value. It measures the maximum amount of force needed (or psi when foot area is taken into consideration) to separate the probe from the material. The work of adhesion is the total area under the curve of FIG. 11A (above the X axis). This property should have units of lb-in (force*distance). It measures the total amount of work done (energy expended) by the retracting force involved in separating the probe from the material (FIG. 10E).

Cohesiveness is the tendency of the material to stick together. For example: taffy is more cohesive than bread. The cohesiveness is measured as the ratio of the area of the right half $A_2$ of the curve of FIG. 11A to that of the left half $A_1$ of the curve with the maximum force point (tack) defining the boundary. If adhesion is low compared with cohesion then the probe is likely to pull off the specimen easily and to remain clean as the product has the ability to hold together. If adhesion is high, out of the maximum range, then sealant is in the range of adhesives.

Figure 11B:
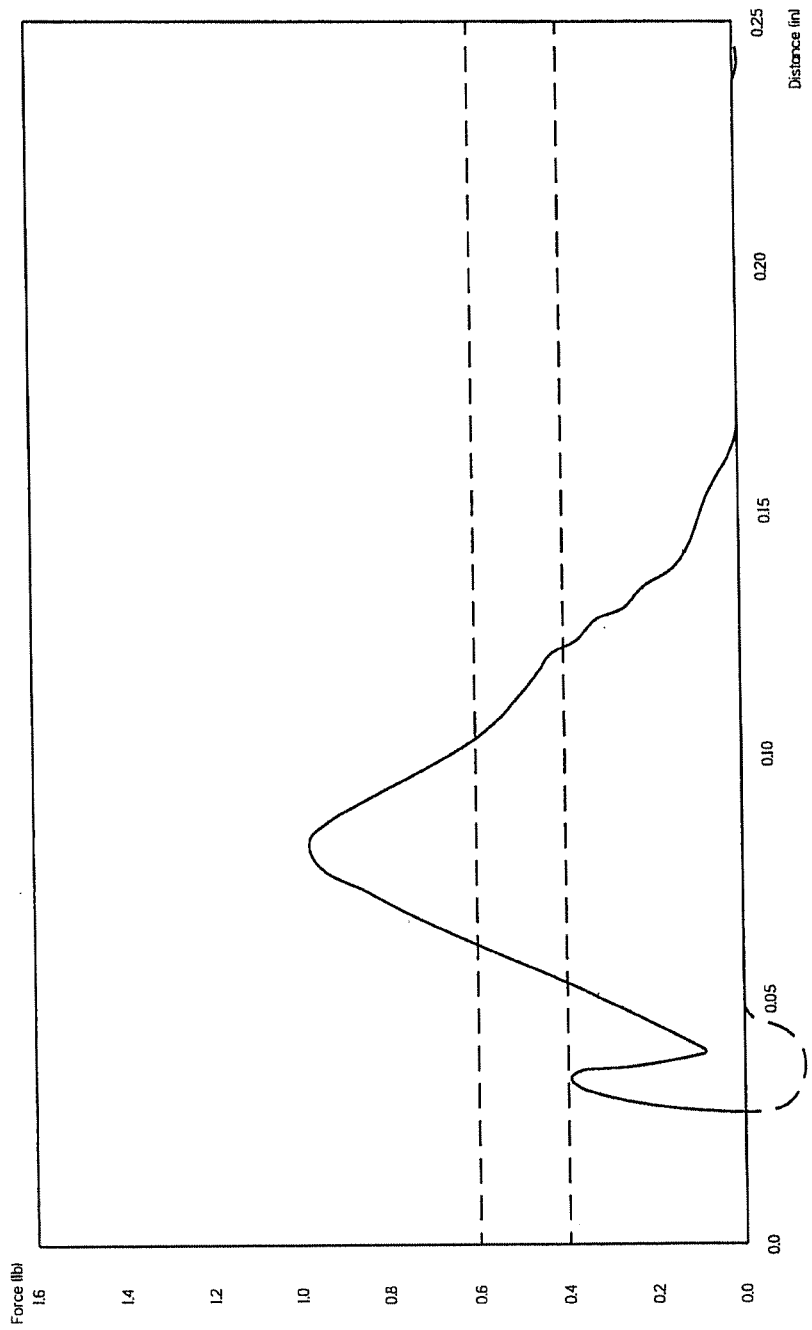

A graph of the tack test for the fireworthy products subject to Tests 1-5 (Applicant's sealant SD#5) and another polyurethane gel and fiberglass skeleton coated with fire retardant (without fireworthiness) designated HT3935-7 by Applicant similarly dimensioned (FIG. 11B) for reference.

|  | Tack | Work of Adhesion | Cohesiveness |
|---|---|---|---|
| SD#5 | 0.91 | 0.051 | 1.188 |
| HT3935-7 | 1.378 | 0.069 | 0.89 |

Results

Following this test method will result in a graph that will record the following—Tack (lb/in$^2$); Work of Adhesion; Cohesiveness.

Applicant Measured the Following Values:
Cohesiveness 0.516
Work of Adhesion 0.948 pound inches
Tack 26.915 pounds/sq. in. (or about 1.4 pounds on a probe with contact area of about 1/16 sq. in.)
Acceptable Ranges:
Tack: 20-30 psi (most preferred), 15-45 psi, 5-50 psi
Work of Adhesion: 0.5-5, 0.1-10
Cohesiveness: 0.25-1, 0.1-3, 0.1-5

Test 6

Test Results: Aviation Fluids Exposure Test

Figures 14A, 14B:
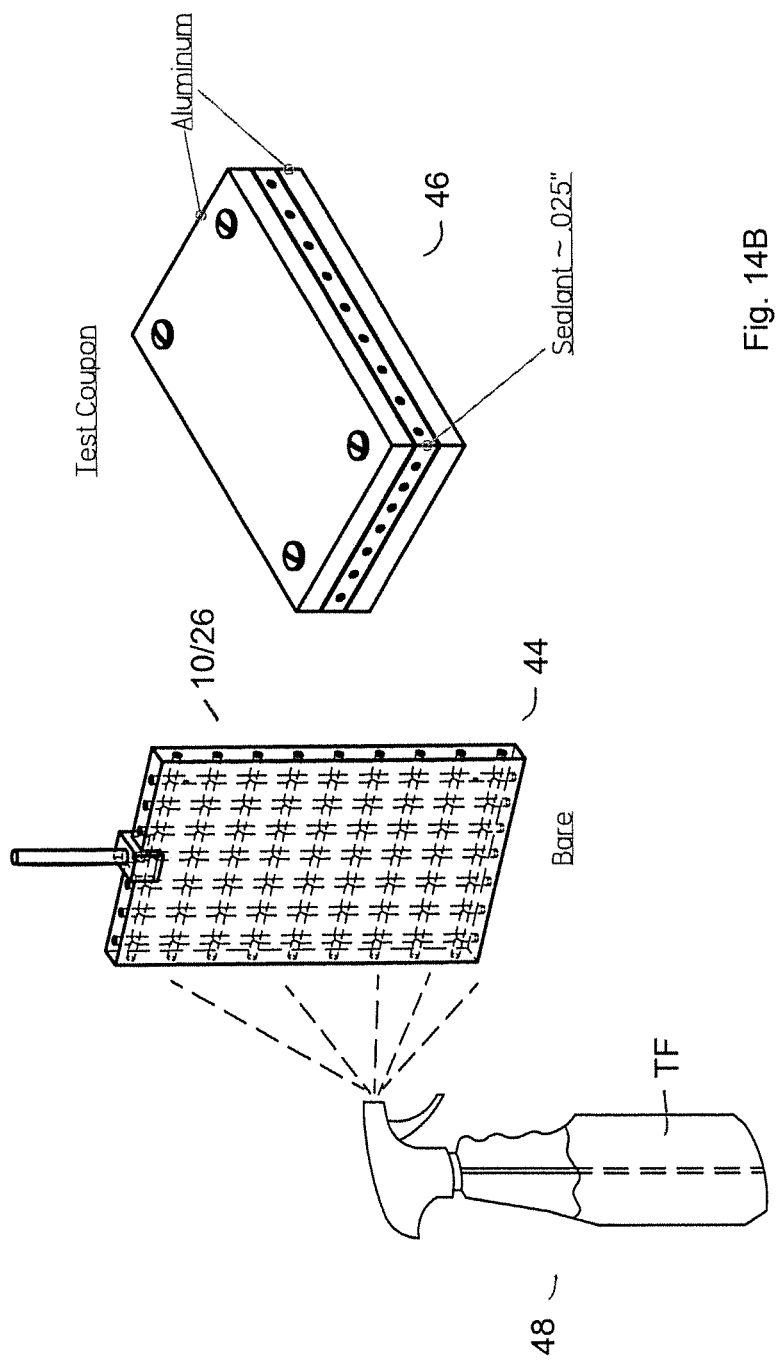
FIGS. 14A and 14B illustrate an Aviation Fluids Exposure Test for testing Applicant's sealants.

Photograph each test assembly (see FIG. 14A, base assembly 44, application FIG. 14B), weigh on an analytical balance, and record the result. Hang test assembly on the spray rack (see FIGS. 14A and 14B). Spray test assembly with test fluid TF from spray bottle 48 every 4 hours for 8 hours, allow to dry for 16 hours and then repeat this cycle two more times. Spray each bare test assembly 44 including sealant 10/26 (FIG. 14A) with nitrogen to remove excess fluid from mesh backing if necessary. Wipe each in-application (aluminum alloy coupon) test assembly 46 including sealant 10/26 (FIG. 14B) with a paper towel to remove excess fluid from coupons if necessary. Photograph each test assembly and weigh on the analytical balance and record the result after each 16 hour dry period. Also, visually note and record any changes in test specimen throughout testing.

Ideally, there should be no fluid on the samples after the drying period and the physical drying before weighing. In practice, there may be some small amount of fluid left on the sample, but may be considered to be "in the noise" and negligible.

The following data is from Applicant's fluids TF exposure test on the fireworthy sealant. The sealant material is sprayed with various aviation fluids. The output data is a percent weight change of the sealant material in both the bare (FIG. 14A) and in application (between two aluminum alloy plates, FIG. 14B) configurations with about a 0.025" "exposure face." A low percent weight change will correspond to good resistance to the fluid in question and a high percent weight change to be the converse. A change in either the positive or negative direction is relevant because it can indicate fluid absorption or material removal respectively. The benefit this test shows is that Applicant's products are resilient enough to continue functioning across a wide variety of aviation environments. The data helps inform Applicant's recommendations for where certain products should be used based on their environment. This data shows these tested products to be resistant to degradation upon exposure to common aviation fluid, based upon 5% or under on both base and application: AGS silicone brake fluid, Royal Purple Synthetic, Isopropyl denatured ethyl, Dynalene EG and PG, and the de-icing fluid. This is based upon these initial tests only.

|  | #5 Bare | #5 In Application |
|---|---|---|
| Jet A Fuel | 12% | 4% |
| Autozone Brake Fluid | 13% | 4% |
| Skydrol LD-4 | 30% | 6% |
| AGS Silicone Brake Fluid | 3% | 3% |
| Royco 782 | 10% | 4% |
| White Mineral Oil | 9% | 5% |
| Royal Purple Synthetic | 5% | 4% |
| Isopropyl | 0% | 1% |
| Denatured Ethyl | 0% | 0% |
| Sky-Kleen | 13% | 4% |
| Dynalene EG | 3% | 4% |
| Dynalene PG | 3% | 4% |
| De-Icing Fluid PA | 3% | 4% |
| De-Ionized Water | 0% | 0% |
| Mobil Aero HF | 15% | 4% |
| 5% NaCl Solution | 2% | 1% |
| Potassium Formate | 4% | 3% |

Figure 8A:
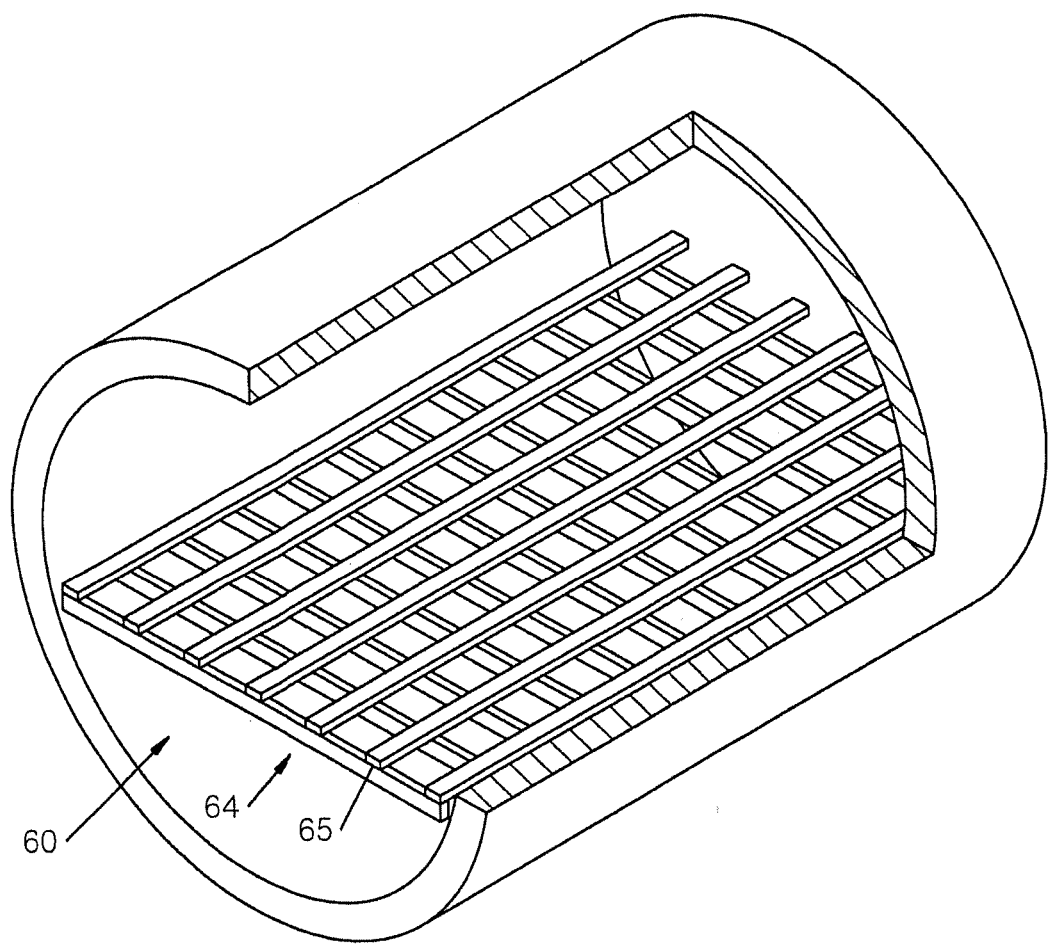
FIGS. 8A, 8B, 8C, and 8D illustrate a use of Applicant's sealant with floorboard assemblies of an aircraft interior.
Figure 8B:
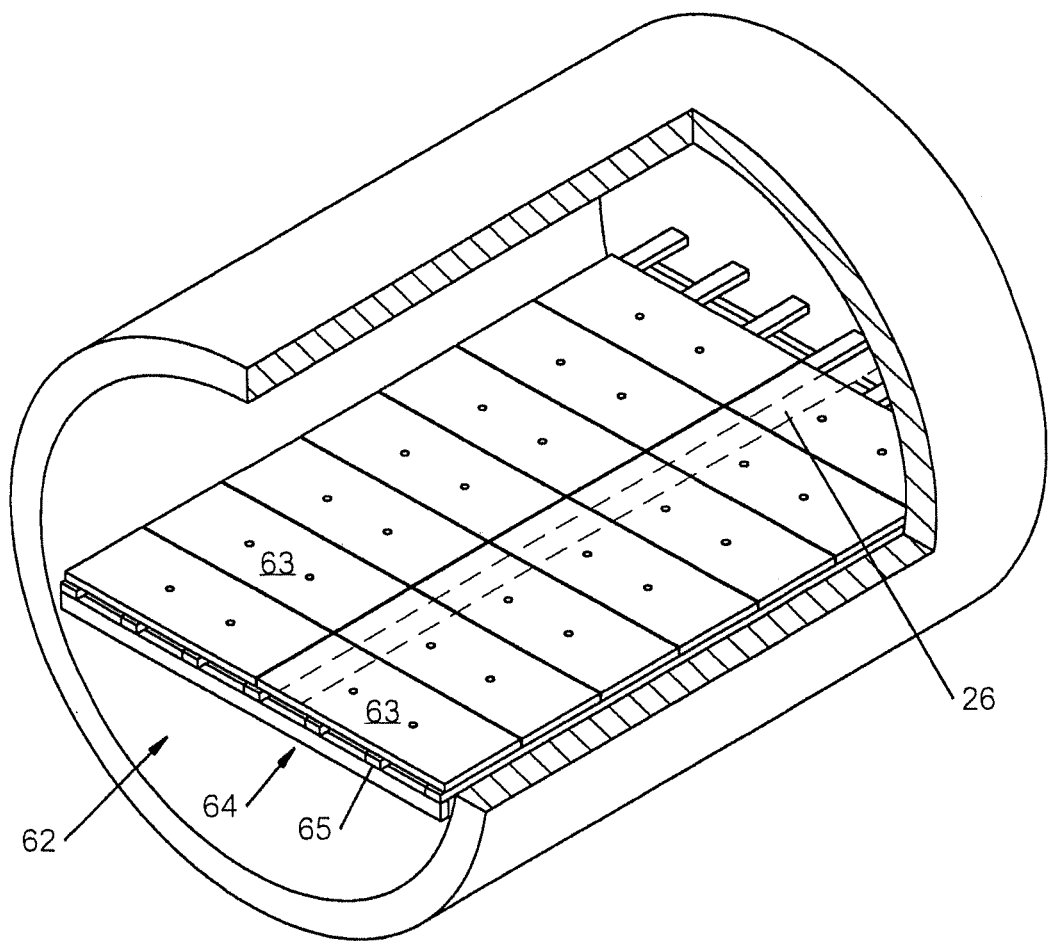
Figure 8C:
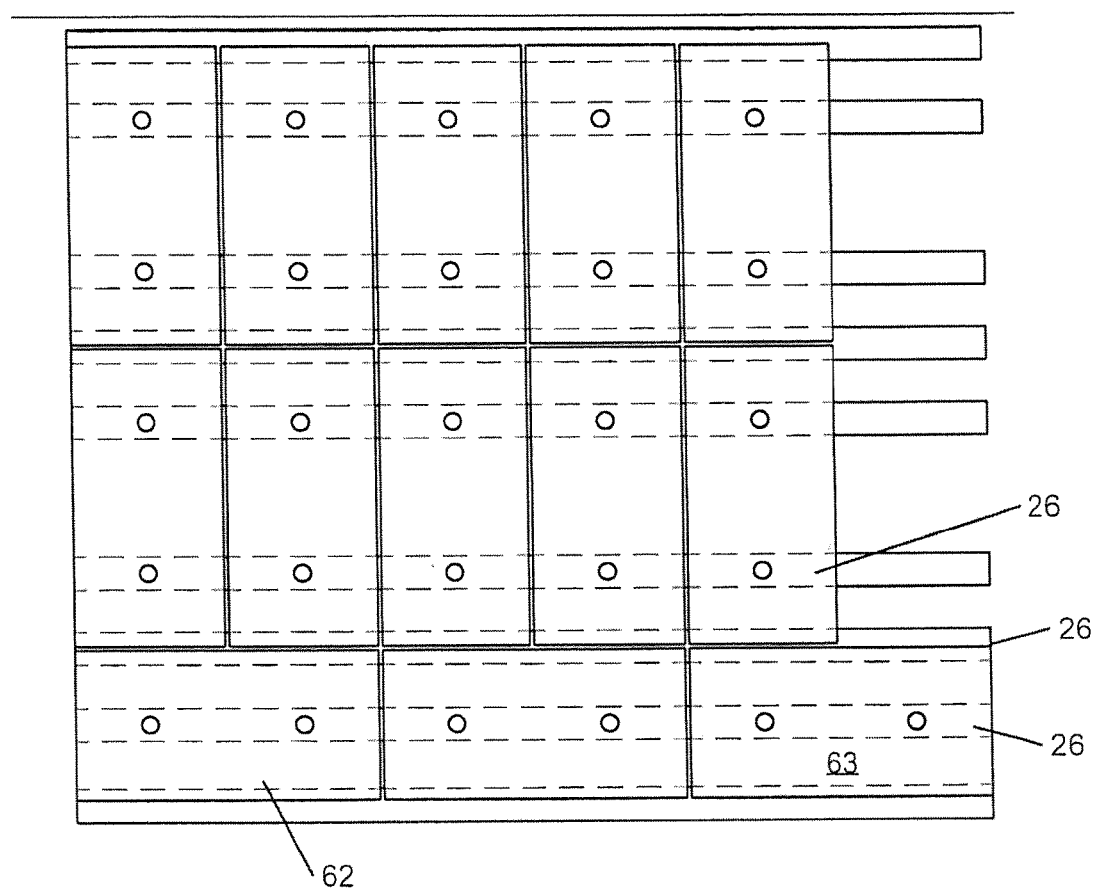
Figure 8D:
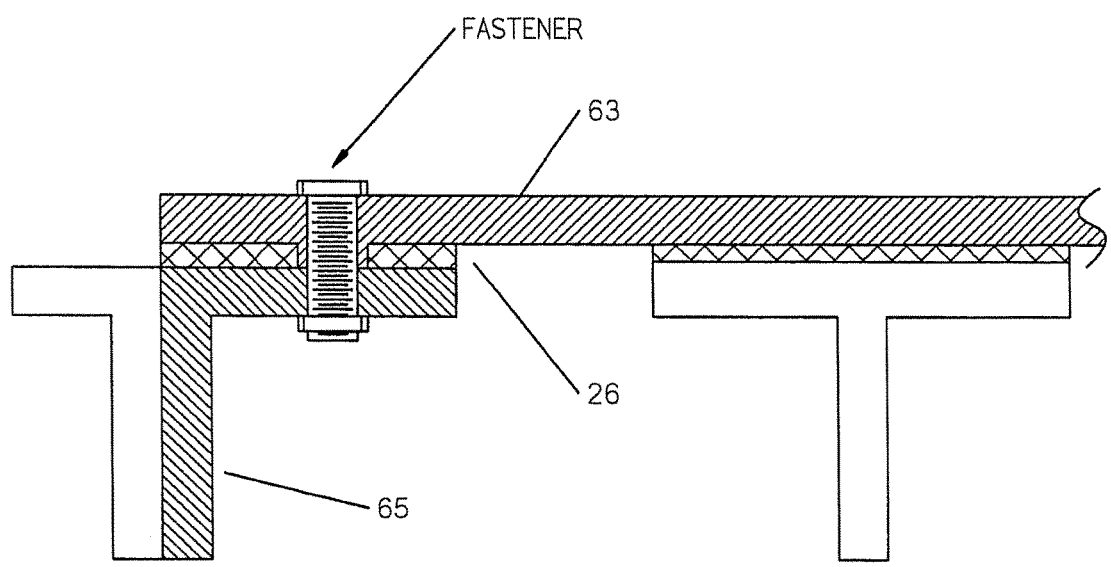

FIGS. 8A-8C illustrate a cabin interior 60 that includes a floorboard assembly 62. Floorboard assembly 62 is provided as a support surface for passengers to walk on and as a support for other structures. Where multiple floorboards 63 join frame subassembly 64, there is typically engagement between the underside of the individual floorboards and the individual members or stringers 65 of the frame subassembly 64. Prior art elastomeric tape has been used to support the floorboards/subassembly joint in an environmentally sealing manner. In one application of tape 26 described herein, the sealant with the novel qualities set forth herein is used between the floorboards and the frame subassembly to impart both an environmental seal as well as beneficial fireworthy properties as set forth herein.

Although the invention has been described with reference to a specific embodiment, this description is not meant to be construed in a limiting sense. On the contrary, various modifications of the disclosed embodiments will become apparent to those skilled in the art upon reference to the description of the invention. It is therefore contemplated that the appended claims will cover such modifications, alternatives, and equivalents that fall within the true spirit and scope of the invention.

The invention claimed is:

1. A sealant comprising a body and a skeleton encapsulated by the body:
    the body comprising a cured, tacky, soft, deformable, non-adhesive gel, the gel body having an upper surface, a lower surface, and a perimeter, wherein the upper and lower surfaces of the gel body, in an uncompressed state, define a body thickness; and
    the skeleton comprising multiple openings for encapsulation by the gel body, the skeleton having an upper surface, a lower surface, and a perimeter;
    the sealant in an uncompressed state dimensioned to fit in a first opening between a wall and an aircraft component surface and deformable when under compression to fit in a second opening, smaller than the first opening;
        wherein the sealant has toxicity limits of less than about: 150 PPM HCN, 1000 PPM CO, 100 PPM NO/NO2, 100 PPM SO2, 100 PPM HF, and 150 PPM HCl under AITM 3-0005, Issue 2; and
        wherein the sealant passes 12 second vertical burn test according to 14 CFR, Part 25—Subpart D, § 25.853 (a) compartment interiors.

2. The sealant of claim 1, wherein the gel is 100% solid (no VOCs).

3. The sealant of claim 1, wherein the sealant has a smoke density of 200 maximum at about 4.0 minutes under AITM2-0007A, Issue 3.

4. The sealant of claim 1, wherein the sealant comprises a two-part polymer, the first part comprising a polyol and the second part comprising an isocyanate, the two parts when combined curing to form the gel of the gel body, and wherein the skeleton is comprised of a nylon, polypropylene, or fiberglass having a thickness less than about 0.033".

5. The sealant of claim 1, wherein the body comprises a polyurethane gel with a molecular weight range is between about 200 to 20,000.

6. The sealant of claim 1, wherein the tackiness of the sealant is between about 10 and 40 psi.

7. The sealant of claim 1, wherein the sealant passes the 3000 hour salt fog test according to ASTMB 117.

8. The sealant of claim 1, wherein the body contains no silicone or silicone oil.

9. The sealant of claim 1, wherein the sealant substantially recovers its original dimensional configuration in less than one minute after 180 days under compression between about 150 and 350 psi.

10. The sealant of claim 1, wherein the sealant has a smoke density of 200 maximum at 4.0 min. under AITM2-0007A, Issue 3.

11. The sealant of claim 10, wherein the sealant comprises a two-part polymer, the first part comprising a polyol and the second part comprising isocyanate, the two parts when combined curing to form the gel of the gel body.

12. The sealant of claim 10, wherein the gel body comprises a cured polyurethane gel of molecular weight between about 200 and 20,000.

13. The sealant of claim 10, wherein the skeleton is either nylon or woven fiberglass and less than about 0.033" thick.

14. The sealant of claim 10, wherein the volume ratio of gel body to skeleton is in the range of about 3 to 1 and 7 to 1.

15. The sealant of claim 10, wherein the cured hardness of the gel body is between about 40 and 150 measured by 35 gr. cone penetrometer.

16. The sealant of claim 10, wherein the body further includes a corrosion inhibiting composition.

17. The sealant of claim 1, wherein the body thickness is greater than a skeleton thickness.

18. The sealant of claim 1, wherein the sealant is resistant to degradation upon exposure to common aviation fluids.

19. The sealant of claim 1, wherein the sealant is a single sided sticky sealant, the sealant provided with a skin on one side of the body, the skin having a surface distal from the body that is non-sticky.

20. A device for providing an environmental seal to an aircraft assembly comprising a first part and a spaced apart second part, the two parts forming a gap, the device comprising:
    a sealant comprising a skeleton and a body encapsulating the skeleton, wherein the body is comprised of a cured polyurethane gel, resulting from a mix of a polyol and isocyanate, the sealant having fireworthiness properties and passing the following tests:
        wherein the sealant has toxicity limits of less than about: 150 PPM HCN, 1000 PPM CO, 100 PPM NO/NO2, 100 PPM SO2, 100 PPM HF, and 150 PPM HCl under AITM 3-0005, Issue 2;
        wherein the sealant passes 12 second vertical burn test according to 14 CFR, Part 25—Subpart D, § 25.853 (a) compartment interiors;
        wherein the sealant has a smoke density of Ds maximum at about 4.0 min. of under 200 AITM2-0007A, Issue 3;
        wherein the skeleton is comprised of a nylon or fiberglass mesh having a thickness less than about 0.033"; and
    the body having a tackiness of between 5 and 50 psi; and wherein the volume of gel/skeleton is in the range of about 3/1 to 7/1.

21. A method for releasably, environmentally sealing a pair of opposing, gap forming, fastener engaging surfaces of aircraft parts, the method comprising the steps of:
    providing an adhesive-free elastomeric, tacky sealant having a layer of polyurethane gel encapsulating a skeleton, the sealant having fireworthiness properties;
    placing the sealant in the gap between the surfaces; and
    compressing the opposing surfaces by tightening the fasteners, and closing the gap contacting the sealant, thereby providing a substantially fluid and air tight seal between the opposed mating surfaces with the sealant substantially filling the gap;
        wherein the sealant has a smoke density of 200 maximum at 4.0 min. under 200 AITM2-0007A, Issue 3;
        wherein the sealant has toxicity limits of less than about: 150 PPM HCN, 1000 PPM CO, 100 PPM NO/NO2, 100 PPM SO2, 100 PPM HF, and 150 PPM HCl under AITM 3-0005, Issue 2; and
        wherein the sealant passes 12 second vertical burn test according to 14 CFR, Part 25—Subpart D, § 25.853 (a) compartment interiors.

22. The method of claim 21, wherein the sealant of the providing step has a tackiness between about 5 and 50 psi.

23. The method of claim 21, wherein the tightening of the compressing step continues until the sealant visibly deforms.

24. The method of claim 21, wherein the body comprises a polyurethane gel and the molecular weight range is between about 200 to 20,000.

25. The method of claim 21, wherein the sealant passes the 3000 hour salt fog test according to ASTMB 117.

26. The method of claim 21, wherein the body of sealant is deformable under compression.

27. The method of claim 21, wherein the sealant substantially recovers its original dimensional configuration after 180 days under compression between about 150 and 350 psi.

28. The method of claim 21, wherein the skeleton is either nylon or woven fiberglass and less than about 0.033" thick.

29. The method of claim 21, wherein the sealant is resistant to degradation upon exposure to common aviation fluids.

30. The method of claim 21, wherein the sealant is a single sided sticky sealant, the sealant provided with a skin on one side of the body, the skin having a surface distal from the body that is non-sticky.

\* \* \* \* \*